(12) United States Patent
Morita

(10) Patent No.: US 8,767,057 B2
(45) Date of Patent: Jul. 1, 2014

(54) IMAGE PROCESSING DEVICE, IMAGE PROCESSING METHOD, AND PROGRAM

(75) Inventor: Yasunori Morita, Hachioji (JP)

(73) Assignee: Olympus Corporation, Tokyo (JP)

( * ) Notice: Subject to any disclaimer, the term of this patent is extended or adjusted under 35 U.S.C. 154(b) by 589 days.

(21) Appl. No.: 13/070,762

(22) Filed: Mar. 24, 2011

(65) Prior Publication Data

US 2011/0242301 A1 Oct. 6, 2011

(30) Foreign Application Priority Data

Mar. 30, 2010 (JP) ................................. 2010-076760

(51) Int. Cl.
*H04N 11/02* (2006.01)
*A61B 1/00* (2006.01)
*A61B 1/04* (2006.01)
*A61B 5/06* (2006.01)
*A61B 5/00* (2006.01)

(52) U.S. Cl.
CPC ......... *A61B 1/00009* (2013.01); *A61B 1/00128* (2013.01); *A61B 1/041* (2013.01); *A61B 5/06* (2013.01); *A61B 5/4255* (2013.01)
USPC ............. 348/65; 382/107; 382/128; 600/428; 606/130

(58) Field of Classification Search
USPC ............ 382/107–128; 600/109–429; 606/130
See application file for complete search history.

(56) References Cited

U.S. PATENT DOCUMENTS

| 7,319,781 B2* | 1/2008 | Chen et al. ..................... 382/128 |
| 7,761,134 B2* | 7/2010 | Horn et al. ..................... 600/424 |
| 8,107,704 B2* | 1/2012 | Kanda et al. .................. 382/128 |
| 2004/0092825 A1* | 5/2004 | Madar et al. ................... 600/473 |
| 2008/0262297 A1* | 10/2008 | Gilboa et al. .................. 600/109 |
| 2008/0287783 A1* | 11/2008 | Anderson ....................... 600/429 |
| 2009/0299142 A1* | 12/2009 | Uchiyama et al. ............. 600/118 |
| 2009/0303319 A1* | 12/2009 | Sato et al. ........................ 348/65 |

FOREIGN PATENT DOCUMENTS

| JP | 2002-238839 A | 8/2002 |
| JP | 2004-239791 | 8/2004 |
| JP | 2005-168524 A | 6/2005 |
| JP | 2005-522274 A | 7/2005 |
| JP | 2006-149481 | 6/2006 |
| JP | 2008-100075 A | 5/2008 |
| JP | 2010-63484 A | 3/2010 |

OTHER PUBLICATIONS

English abstract only of WO 03/086498.
Japanese Office Action dated Jan. 7, 2014 from related Japanese Application No. 2010-076760, together with an English language translation.

* cited by examiner

*Primary Examiner* — William C Vaughn, Jr.
*Assistant Examiner* — Luis M Perez
(74) *Attorney, Agent, or Firm* — Scully, Scott, Murphy & Presser, P.C.

(57) ABSTRACT

An image processing device includes an image acquisition section that acquires an image that has been acquired by imaging a tissue using an endoscope apparatus, an in vivo position identification information acquisition section that acquires in vivo position identification information that specifies an in vivo position of the endoscope apparatus when the image has been acquired, a in vivo model acquisition section that acquires a in vivo model that is a model of the tissue, an on-model position determination section that specifies an on-model position that corresponds to the position specified by the in vivo position identification information on the acquired in vivo model, and a linking section that links information about the acquired image to the specified on-model position.

32 Claims, 21 Drawing Sheets

FIG. 4
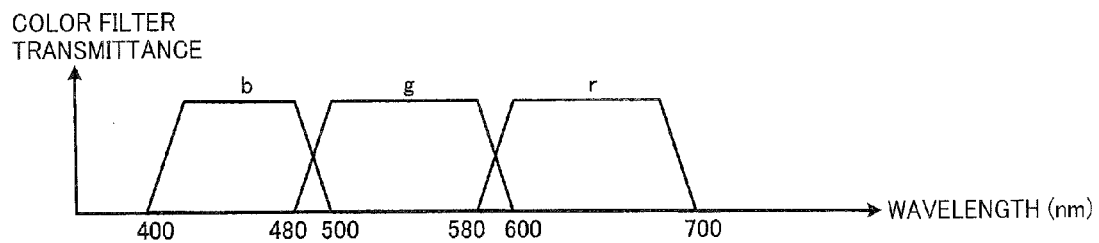
FIG. 5
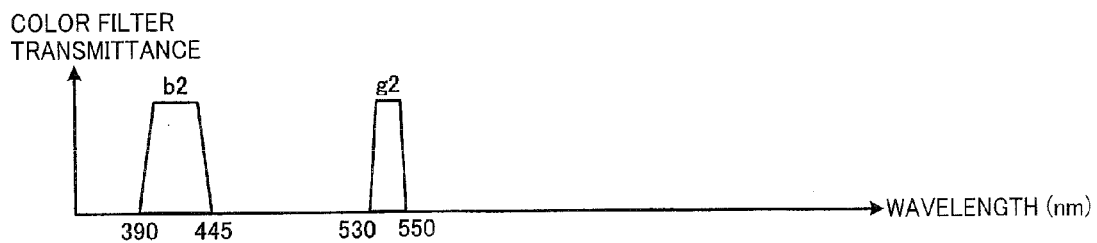
FIG. 6

FIG. 11A
FIG. 11B
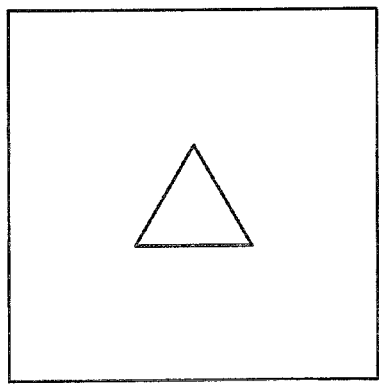
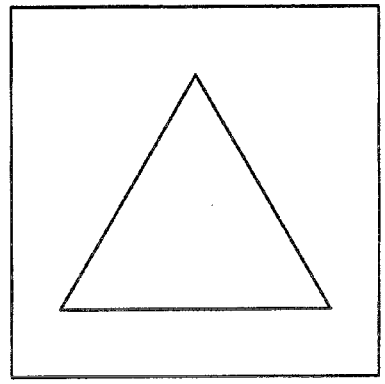
FIG. 12
| MAGNIFICATION | MOVING DISTANCE (mm) |
|---|---|
| P1 | Q1 |
| P2 | Q2 |
| P3 | Q3 |
| ⋮ | ⋮ |

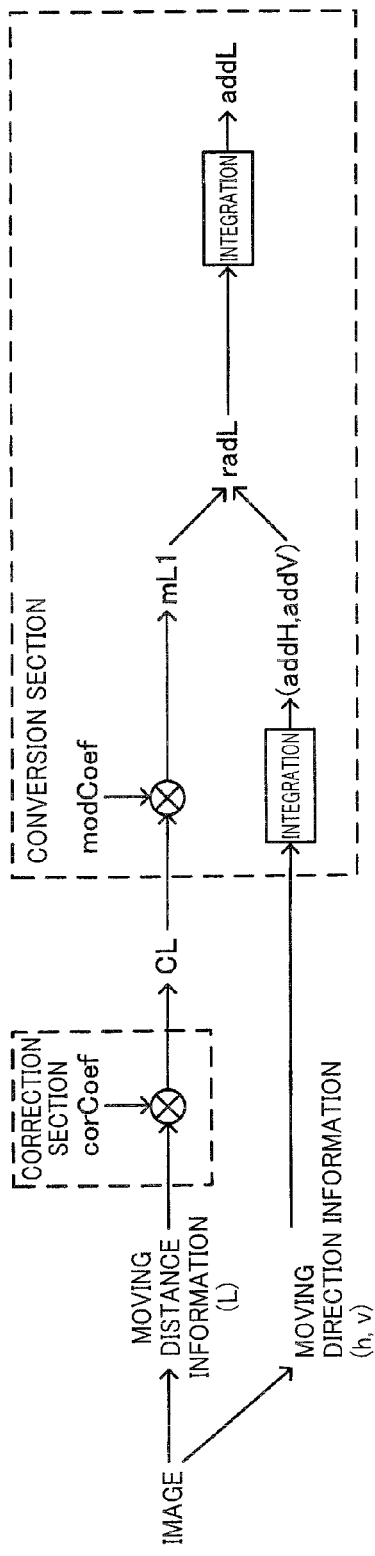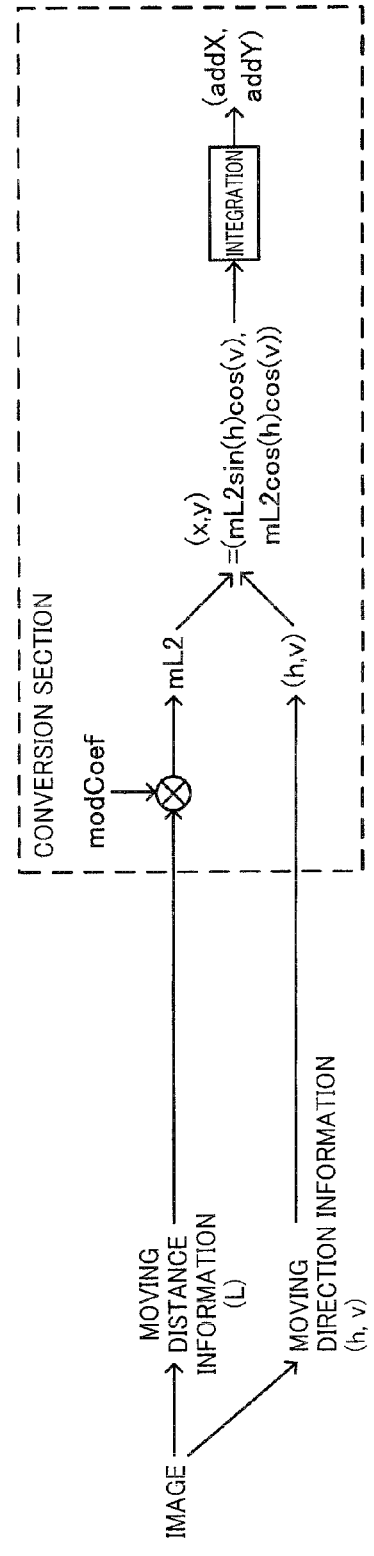

US 8,767,057 B2

IMAGE PROCESSING DEVICE, IMAGE PROCESSING METHOD, AND PROGRAM

Japanese Patent Application No. 2010-076760 filed on Mar. 30, 2010, is hereby incorporated by reference in its entirety.

BACKGROUND

The present invention relates to an image processing device, an image processing method, a program, and the like.

A medical instrument (e.g., endoscope apparatus) that is inserted into a body cavity (e.g., digestive tract), and used for diagnosis, medical treatment, and the like has been known. When performing examination or an operation on a tissue using such a medical instrument, the operator presumes the position of the currently observed site taking account of the known positional relationship between each site (organs and tissues) inside the body. Technology that displays the in vivo position of an endoscope apparatus during examination or an operation in order to support the examination or operation has been proposed.

For example, JP-A-2006-149481 discloses technology that detects the position of the end of an ultrasonic endoscope, and displays a guide image that corresponds to the in vivo position of the ultrasonic endoscope.

JP-A-2006-149481 provides a sample point position detection means that detects the position of a sample point of a tissue, and compares the position of the sample point detected by the sample point position detection means with the position of a feature point on reference image data stored in an image information storage means when creating the guide image. JP-A-2006-149481 also provides a posture detection means that detects the position or the posture of a tissue, and is fitted on a subject. The guide image is created while correcting a change in posture of the subject by correcting the position of the sample point detected by the sample point position detection means based on the position or the direction of the subject detected by the posture detection means.

SUMMARY

According to one aspect of the invention, there is provided an image processing device comprising:

an image acquisition section that acquires an image that has been acquired by imaging a tissue using an endoscope apparatus;

an in vivo position identification information acquisition section that acquires in vivo position identification information that specifies an in vivo position of the endoscope apparatus when the image has been acquired;

an in vivo model acquisition section that acquires an in vivo model that is a model of the tissue;

an on-model position determination section that specifies an on-model position that corresponds to the position specified by the in vivo position identification information on the acquired in vivo model; and a linking section that links information about the acquired image to the specified on-model position.

According to another aspect of the invention, there is an image processing method comprising:

acquiring an image that has been acquired by imaging a tissue using an endoscope apparatus;

acquiring in vivo position identification information that specifies an in vivo position of the endoscope apparatus when the image has been acquired;

acquiring an in vivo model that is a model of the tissue;

specifying an on-model position that corresponds to the position specified by the in vivo position identification information on the acquired site model; and linking information about the acquired image to the specified on-model position.

According to another aspect of the invention, there is an A program that is stored in an information storage medium, the program causing a computer to function as:

an image acquisition section that acquires an image that has been acquired by imaging a tissue using an endoscope apparatus;

an in vivo position identification information acquisition section that acquires in vivo position identification information that specifies an in vivo position of the endoscope apparatus when the image has been acquired;

an in vivo model acquisition section that acquires an in vivo model that is a model of the tissue;

an on-model position determination section that specifies an on-model position that corresponds to the position specified by the in vivo position identification information on the acquired site model; and a linking section that links information about the acquired image to the specified on-model position.

BRIEF DESCRIPTION OF THE DRAWINGS

FIG. 4 shows the spectral characteristics of color filters r, g, and b.

FIG. 5 is a view illustrative of color filters g2 and b2.

FIG. 6 shows the spectral characteristics of color filters g2 and b2.

FIG. 11A shows an image acquired at a first timing, and FIG. 11B is an example of an image acquired at a second timing and having a shape similar to that of the image acquired at the first timing.

FIG. 12 shows the relationship between the magnification and the moving distance of an acquired image.

FIG. 15A is a view illustrative of a correction process and a conversion process when using a shortening technique, and FIG. 15B is a view illustrative of a correction process and a conversion process when a shortening technique is not used.

DESCRIPTION OF EXEMPLARY EMBODIMENTS

Several aspects of the invention may provide an image processing device, an image processing method, a program, and the like that implement accurate coincidence between the in vivo position of an endoscope apparatus and the position of the endoscope apparatus on an in vivo model image (guide image).

Several aspects of the invention may provide an image processing device, an image processing method, a program, and the like that enable the position of an endoscope apparatus on a guide image to accurately coincide with the in vivo position of the endoscope apparatus without using an extensive apparatus that detects the in vivo position of the endoscope apparatus.

According to one embodiment of the invention, there is provided an image processing device comprising:

an image acquisition section that acquires an image that has been acquired by imaging a tissue using an endoscope apparatus;

an in vivo position identification information acquisition section that acquires in vivo position identification information that specifies an in vivo position of the endoscope apparatus when the image has been acquired;

an in vivo model acquisition section that acquires an in vivo model that is a model of the tissue;

an on-model position determination section that specifies an on-model position that corresponds to the position specified by the in vivo position identification information on the acquired site model; and a linking section that links information about the acquired image to the specified on-model position.

According to this embodiment, the on-model position that corresponds to the in vivo position of the endoscope apparatus when the image has been acquired is specified based on the in vivo position identification information. The information about the acquired image is linked to the specified on-model position. This makes it possible to display a model image (guide image) in which the on-model position of the endoscope apparatus accurately coincides with the in vivo position of the endoscope apparatus.

Embodiments of the invention are described below. Note that the following embodiments do not in any way limit the scope of the invention laid out in the claims. Note also that all elements of the following embodiments should not necessarily be taken as essential requirements for the invention.

1. Method

Figure 1:
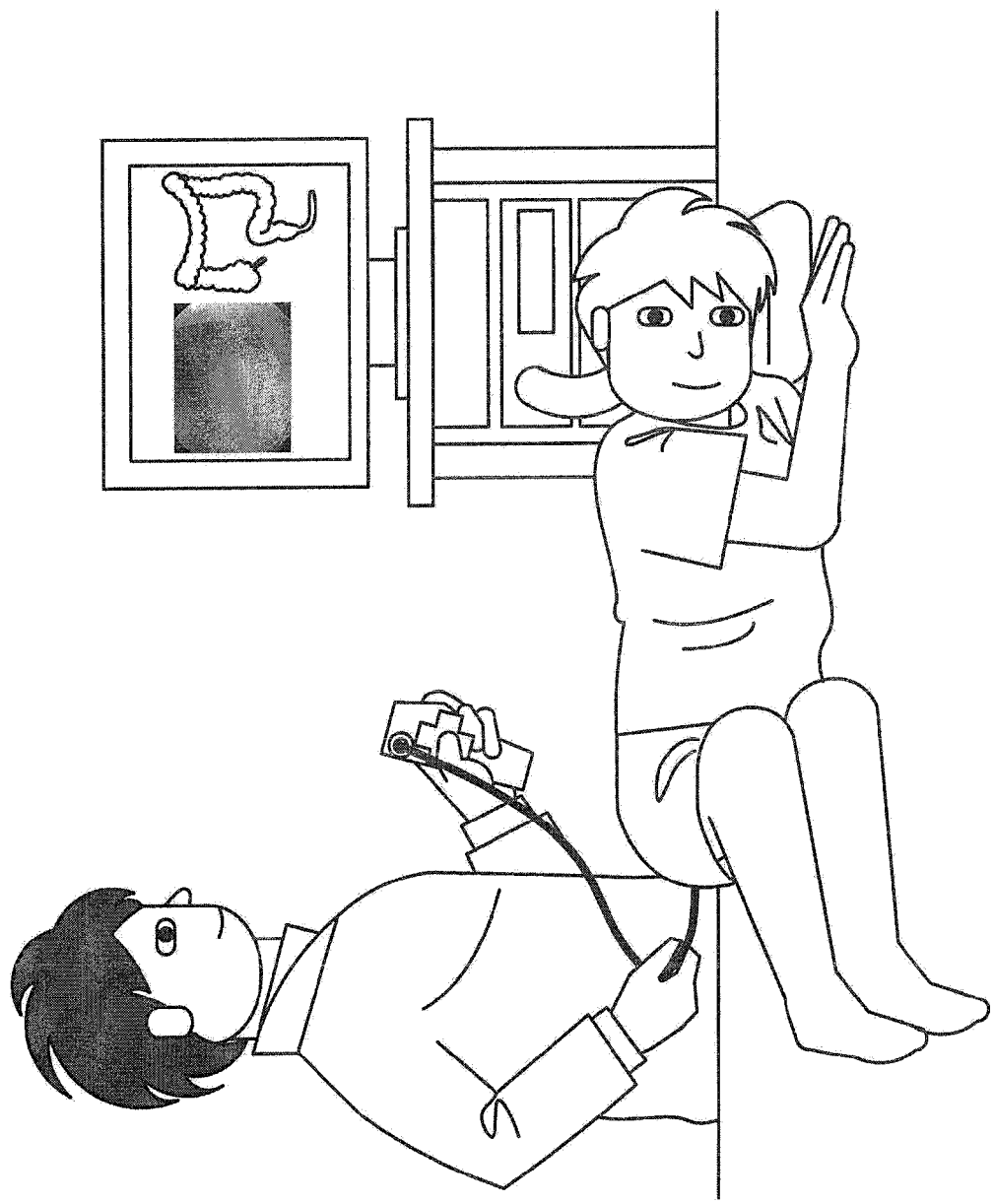
FIG. 1 shows an example of a display method according to one embodiment of the invention.

A method according to one embodiment of the invention is described below. FIG. 1 shows an example of a display method according to one embodiment of the invention. As shown in FIG. 1, an in vivo image acquired (imaged) by an insertion section (imaging section) of an endoscope apparatus and a model image (i.e., model of in vivo site) are displayed on a display section of an endoscope apparatus including an image processing device according to one embodiment of the invention.

Figure 17:
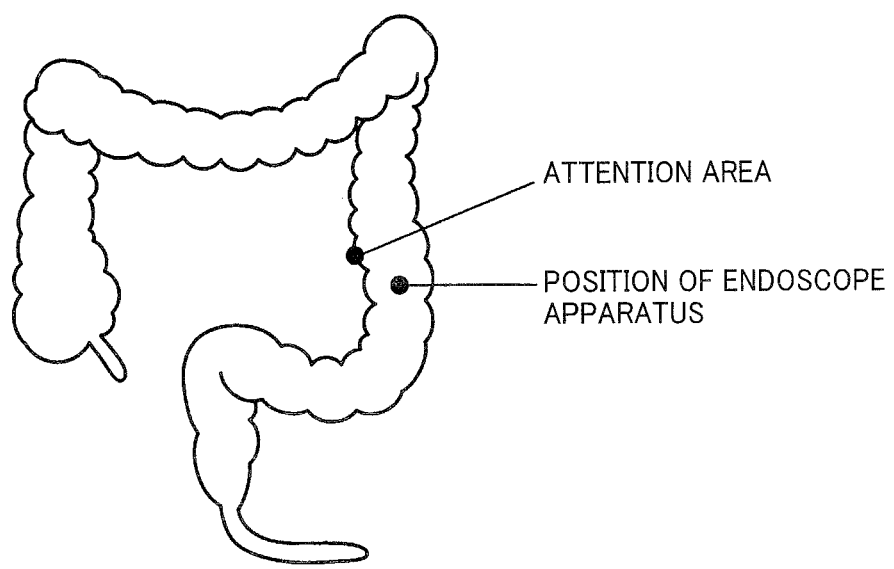
FIG. 17 shows an example of displaying indicators that indicate an attention area and the position of an endoscope apparatus on an in vivo model.

As shown in FIG. 17, an indicator that indicates the in vivo position of the insertion section of the endoscope apparatus is displayed on the model image. An indicator that indicates an attention area (e.g., lesion area) may also be displayed on the model image.

If the position of the endoscope apparatus on the model image accurately coincides with the in vivo position of the endoscope apparatus, the current position of the endoscope apparatus, the position of the lesion area, and the like can be accurately determined. This makes it possible for the doctor to easily perform examination.

Specifically, movement information (e.g., moving distance and moving direction) about the endoscope apparatus is acquired as in vivo position identification information by an arbitrary method. A first embodiment illustrates a method that acquires the in vivo position identification information based on an image acquired by the insertion section (imaging section) of the endoscope apparatus. A second embodiment illustrates a method that acquires the in viva position identification information based on sensor information from a sensor.

The acquired in vivo position identification information corresponds to the actual moving distance of the insertion section of the endoscope apparatus. However, it is problematic to calculate the position on the model (hereinafter referred to as "on-model position") that corresponds to the in vivo position of the endoscope apparatus by directly using the in vivo position identification information.

Figure 2A:
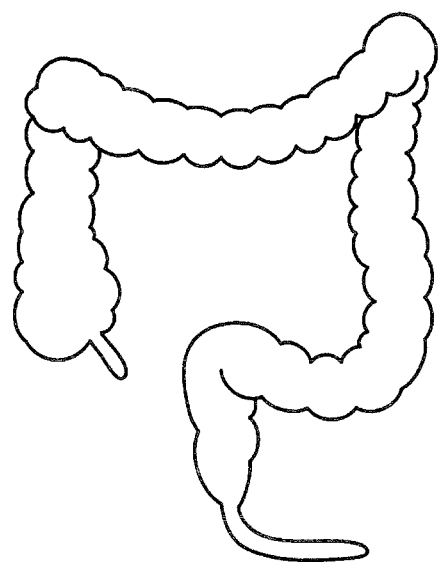
FIG. 2A is a view showing a normal state of a large intestine.

This is because a shortening technique or the like is used when inserting the endoscope into the large intestine. It is difficult to insert the endoscope into the large intestine since a twist operation and a pullback operation are normally required, and a loop state (i.e., the endoscope is inserted in a bent state) easily occurs. The shortening technique solves this problem. Specifically, the shortening technique facilitates insertion of the endoscope by linearly extending a curved region (see FIGS. 2A and 2B). Therefore, even if the actual moving distance (distance indicated by in vivo position identification information) is short, the endoscope may have considerably advanced through the curved region on the model.

Accordingly, it is necessary to calculate the in vivo position identification information (corrected in vivo position identification information) after correcting the difference due to the shortening technique or the like. Moreover, since the in vivo position identification information is movement information and the like corresponding to the actual scale, the in vivo position identification information must be converted into a distance on the model. The above method is described in connection with the first embodiment.

Note that the correction process and the conversion process may be performed in an arbitrary order. A third embodiment illustrates a method that performs the conversion process before the correction process.

The in vivo model may be acquired by various methods. A fourth embodiment illustrates an example using a capsule endoscope, and a fifth embodiment illustrates an example using a CT scanner.

2. First Embodiment

An endoscope apparatus that includes an image processing device according to a first embodiment of the invention is described below with reference to FIG. 3. The endoscope apparatus that includes the image processing device according to this embodiment includes a light source section 100, an insertion section 200, an image processing section 300, a display section 400, and an external I/F section 500.

The light source section 100 includes a white light source 110 that emits (generates) white light, and a condenser lens 120 that focuses white light on a light guide fiber 210.

The insertion section 200 is formed to be elongated and flexible (i.e., can be curved) so that the insertion section 200 can be inserted into a body cavity, for example. The insertion section 200 includes the light guide fiber 210 that guides light focused by the light source section 100, an illumination lens 220 that diffuses light that has been guided by the light guide fiber 210, and illuminates an observation target, an objective lens 230 that focuses light reflected by the observation target, a half mirror 240 that separates the focused reflected light in two, and a first imaging element 250 and a second imaging element 260 that detect the separated reflected light.

The imaging element 250 includes a Bayer color filter array that is used to photograph a normal light image. Color filters R, G, and B of the first imaging element 250 have spectral characteristics shown in FIG. 4, for example. The second imaging element 260 photographs a narrow-band image. As shown in FIG. 5, the second imaging element 260 has a configuration in which color filters g2 that allow narrow-band light G2 to pass through and color filters b2 that allow narrow-band light B2 to pass through are disposed in a checkered pattern, for example. As shown in FIG. 6, the color filter g2 of the second imaging element 260 allows light within a wavelength band of 530 to 550 nm to pass through, and the color filter b2 of the second imaging element 260 allows light within a wavelength band of 390 to 445 nm to pass through, for example.

The image processing section 300 (image processing device) includes AD conversion sections 310a and 310b, a normal light image acquisition section 320, a special light image acquisition section 330, a guide image generation section 340, and a control section 350. The control section 350 is bidirectionally connected to the normal light image acquisition section 320, the special light image acquisition section 330, and the guide image generation section 340, and controls the normal light image acquisition section 320, the special light image acquisition section 330, and the guide image generation section 340.

The external I/F section 500 is an interface that allows the user to perform an input operation or the like on the endoscope apparatus. The external I/F section 500 includes a power supply switch (power supply ON/OFF switch), a shutter button (photographing operation start button), a mode (e.g., photographing mode) change button, and the like. The external I/F section 500 outputs input information to the control section 350.

The AD conversion section 310a converts an analog signal output from the first imaging element 250 into a digital signal, and outputs the digital signal. The AD conversion section 310b converts an analog signal output from the second imaging element 260 into a digital signal, and outputs the digital signal.

The normal light image acquisition section 320 acquires a normal light image from the digital signal output from the AD conversion section 310a, for example. The special light image acquisition section 330 acquires a special light image from the digital signal output from the AD conversion section 310b, for example. The normal light image acquisition section 320 and the special light image acquisition section 330 are described in detail later.

The normal light image acquired by the normal light image acquisition section 320 is output to the display section 400 as an observation image. The normal light image acquired by the normal light image acquisition section 320 and the special light image acquired by the special light image acquisition section 330 are output to the guide image generation section 340. The guide image generation section 340 generates a guide image, and outputs the guide image to the image display section 400. The guide image generation section 340 is described in detail later.

Figure 7:
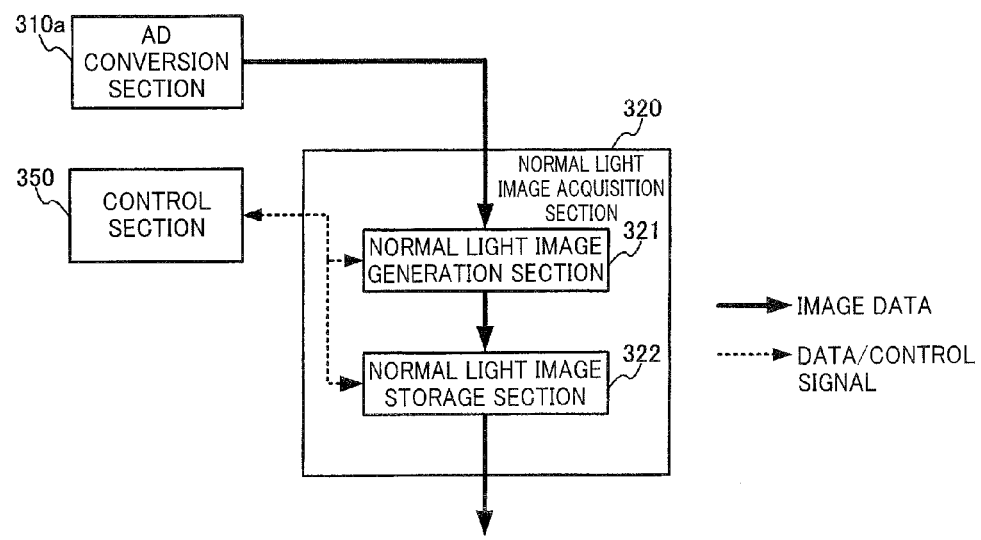
FIG. 7 shows a configuration example of a normal light image acquisition section.

The normal light image acquisition section 320 is described below with reference to FIG. 7. The normal light image acquisition section 320 includes a normal light image generation section 321 and a normal light image storage section 322. When a digital signal converted by the AD conversion section 310a has been input to the normal light image generation section 321, the normal light image generation section 321 performs an image processing on the digital signal to generate a normal light image. Specifically, the normal light image generation section 321 performs an interpolation process, a white balance process, a color conversion process, a grayscale transformation process, and the like on the digital signal to generate a normal light image, and outputs the normal light image. The normal light image storage section 322 stores the normal light image output from the normal light image generation section 321.

Figure 8:
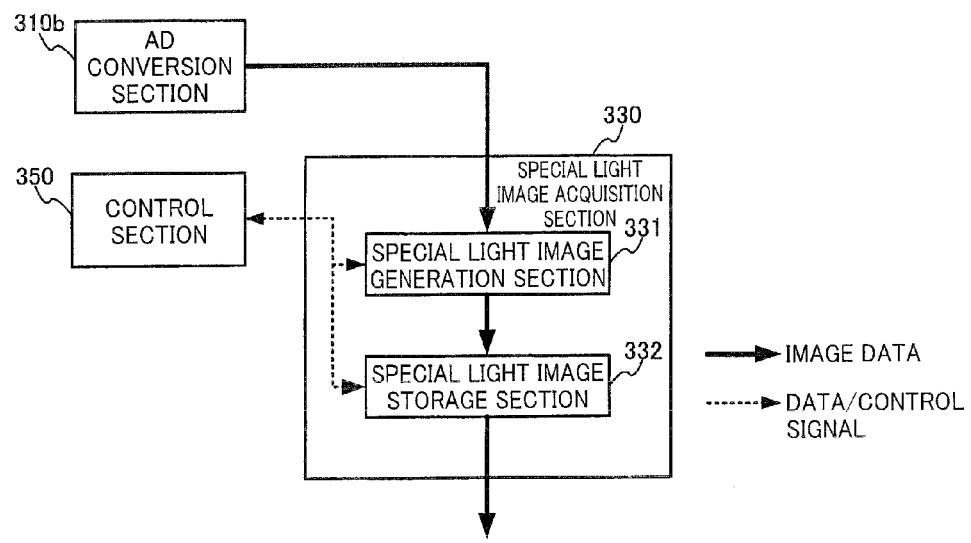
FIG. 8 shows a configuration example of a special light image acquisition section.

The special light image acquisition section 330 is described below with reference to FIG. 8. The special light image acquisition section 330 includes a special light image generation section 331 and a special light image storage section 332. When a digital signal converted by the AD conversion section 310b has been input to the special light image generation section 331, the special light image generation section 331 performs image processing on the digital signal to generate a special light image. In this embodiment, the special light image is a narrow-band image.

The special light image generation section 331 generates a narrow-band image as follows. The digital image signal input to the special light image generation section has a configuration in which the color filters g2 and b2 are disposed in a checkered pattern (see FIG. 5). The special light image generation section 331 performs an interpolation process on the image signal to generate a G2 image in which all of the pixels have a signal value of the filter g2, and a B2 image in which all of the pixels have a signal value of the filter b2. The pixel value calculated by the interpolation process may be the average value of the four peripheral pixels, for example. For example, the pixel value b2(1,1) at the position g2(1,1) and the pixel value g2(1,2) at the position b2(1,2) shown in FIG. 5 are calculated by the following expressions (1) and (2).

$$b2(1,1)=[b2(0,1)+b2(1,0)+b2(1,2)+b2(2,1)]/4 \qquad (1)$$

$$g2(1,2)=[g2(0,2)+g2(1,1)+g2(1,3)+g2(2,2)]/4 \qquad (2)$$

A color image having R, G, and B channels is generated from the G2 image and the B2 image obtained by the interpolation process. For example, a color image is generated by inputting the G2 image to the R channel of the color image, and inputting the B2 image to the G channel and the B channel of the color image. The special light image generation section 331 performs a white balance process, a grayscale transformation process, and the like on the generated color image, and outputs the resulting color image as a narrow-band image. The special light image storage section 332 stores the special light image output from the special light image generation section 331.

Figure 9:
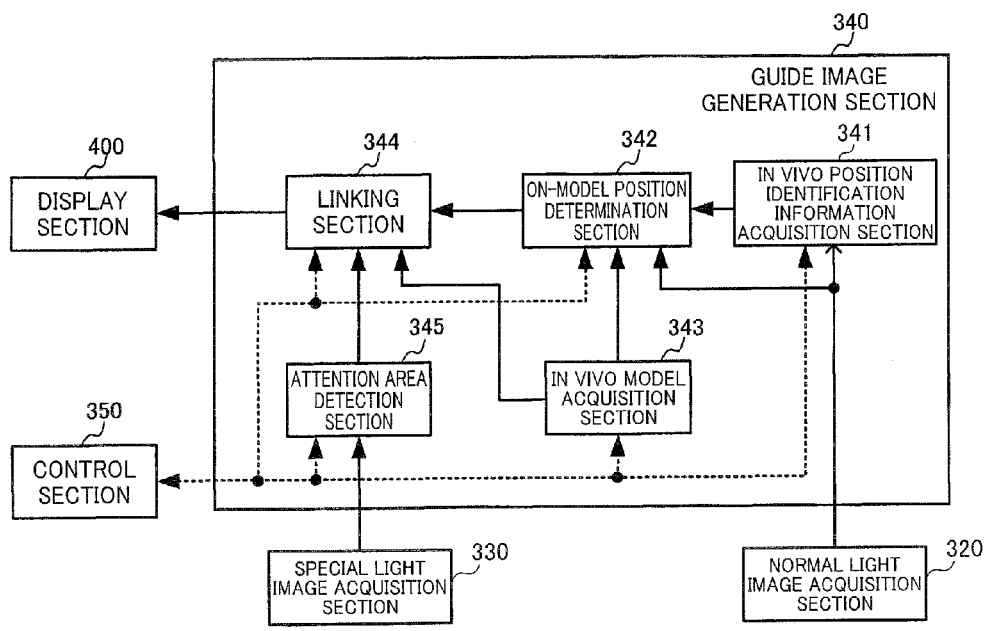
FIG. 9 shows a configuration example of a guide image generation section.

A specific configuration of the guide image generation section 340 is described below. FIG. 9 is a block diagram illustrative of an example of the configuration of the guide image generation section 340 according to the first embodiment. The guide image generation section 340 includes an in vivo position identification information acquisition section 341, an in vivo model acquisition section 343, an on-model position determination section 342, a linking section 344, and an attention area detection section 345.

The image signal from the normal light image acquisition section 320 is output to the in vivo position identification information acquisition section 341 and the on-model position determination section 342. The in vivo position identification information acquisition section 341 is connected to the on-model position determination section 342. The in vivo model acquisition section 343 is connected to the on-model position determination section 342 and the linking section 344. The image signal from the special light image acquisition section 330 is output to the attention area detection section 345. The attention area detection section 345 is connected to the linking section 344. The linking section 344 is connected to the display section 400. The control section 350 is bidirectionally connected to the in vivo position identification information acquisition section 341, the on-model position determination section 342, the in vivo model acquisition section 343, the linking section 344, and the attention area detection section 345, and controls the in vivo position identification information acquisition section 341, the on-model position determination section 342, the in vivo model acquisition section 343, the linking section 344, and the attention area detection section 345.

Figure 10:
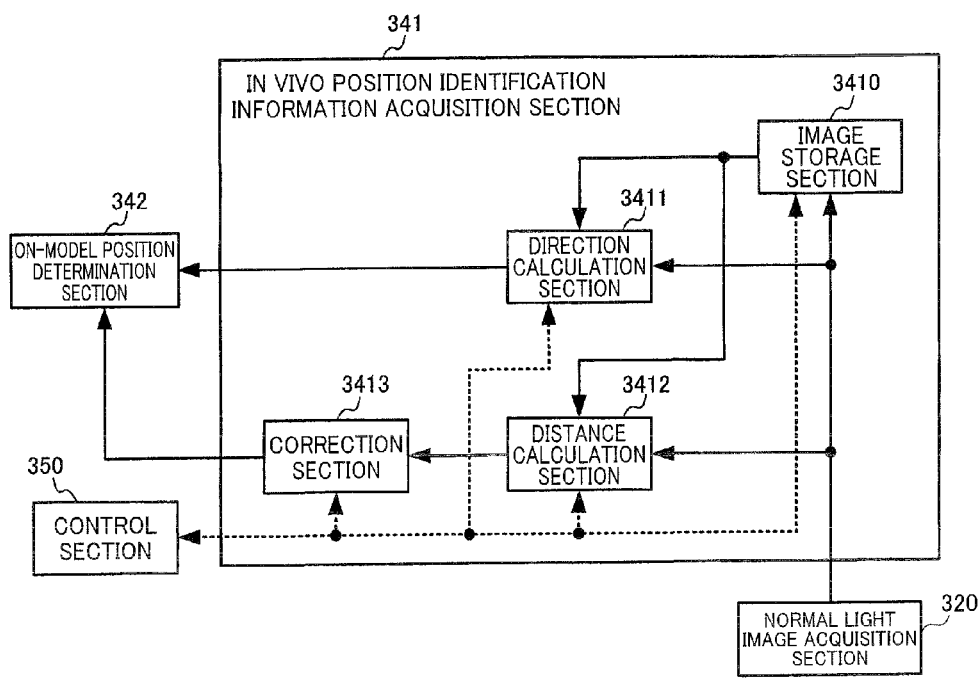
FIG. 10 shows a configuration example of an in vivo position identification information acquisition section.

The in vivo position identification information acquisition section 341 acquires the moving distance of the endoscope apparatus and the in vivo moving direction of the endoscope apparatus as information that specifies the in vivo position of the endoscope apparatus when the image has been acquired (i.e., when the in vivo site has been imaged), under control of the control section 350. A specific configuration of the in vivo position identification information acquisition section 341 is described below. FIG. 10 is a block diagram illustrative of an example of the configuration of the in vivo position identification information acquisition section 341 according to the first embodiment. As shown in FIG. 10, the in vivo position identification information acquisition section 341 includes an image storage section 3410, a distance calculation section 3412, a direction calculation section 3411, and a correction section 3413.

The image storage section 3410 stores the normal light image output from the normal light image acquisition section under control of the control section 350. Specifically, when the normal light image has been input to the image storage section 3410, the normal light image in the preceding frame stored in the image storage section 3410 is output to the distance calculation section 3412 and the direction calculation section 3411, and overwritten with the input normal light image.

The distance calculation section 3412 calculates the in vivo moving distance of the endoscope apparatus as the moving distance of the endoscope apparatus based on the acquired image under control of the control section 350. The distance calculation section 3412 matches a feature point of the image acquired by the normal light image acquisition section 320 with a feature point of the image in the preceding frame stored in the image storage section, and calculates the in vivo moving distance L of the endoscope apparatus from the shape similarity of the feature points. The moving distance L is calculated by a known method. For example, the shape similarity between a feature point extracted from one image and a feature point extracted from another image is determined, as shown in FIGS. 11A and 11B. The moving distance L is calculated referring to a table shown in FIG. 12 that includes the magnification and the moving distance. The moving distance L thus calculated is output to the correction section 3413.

Note that the moving distance may be calculated from the acquired image by a method other than the above matching method. For example, a zoom mechanism may be added to the insertion section 200, and three-dimensional measurement of a monocular image may be performed by utilizing the zoom function. Alternatively, a beam emitting mechanism may be added to the insertion section 200, and three-dimensional measurement may be performed by beam motion estimation (optical flow calculation).

The direction calculation section 3411 calculates the in vivo moving direction of the endoscope apparatus with respect to the measurement start point based on the acquired image under control of the control section 350. Specifically, the direction calculation section 3411 matches the image acquired by the normal light image acquisition section 320 with the image in the preceding frame stored in the image storage section, and calculates the in vivo moving direction (h, v) of the endoscope apparatus based on the matching result. Note that h is the moving angle in the horizontal direction, and v is the moving angle in the vertical direction. The rightward direction with respect to the normal direction of the image plane when the image in the preceding frame has been acquired is positive, and the leftward direction with respect to the normal direction of the image plane when the image in the preceding frame has been acquired is negative. The upward direction with respect to the normal direction of the image plane when the image in the preceding frame has been acquired is positive, and the downward direction with respect to the normal direction of the image plane when the image in the preceding frame has been acquired is negative. The moving direction (h, v) thus calculated is output to the on-model position determination section 342.

The correction section 3413 corrects the in vivo moving distance of the endoscope apparatus calculated by the distance calculation section 3412 based on the structural properties of the entirety or part of the tissue where the endoscope apparatus has moved under control of the control section 350. Specifically, the correction section 3413 increases the moving distance within the entirety or part of a curved tissue that has a curved section into which the endoscope apparatus is inserted using a shortening technique. Specifically, since the shortening technique shortens the intestine by folding the intestine, the moving distance on the in vivo model is longer than the calculated moving distance. A corrected moving distance cL is calculated by the following expression.

$$cL = corCoef \times L \quad (3)$$

Note that corCoef is a coefficient having a value of 1 or more. The coefficient corCoef may be determined by the operator in advance, or may be automatically calculated by the control section 350 based on patient information. The corrected moving distance cL is output to the on-model position determination section 342.

Figure 13:
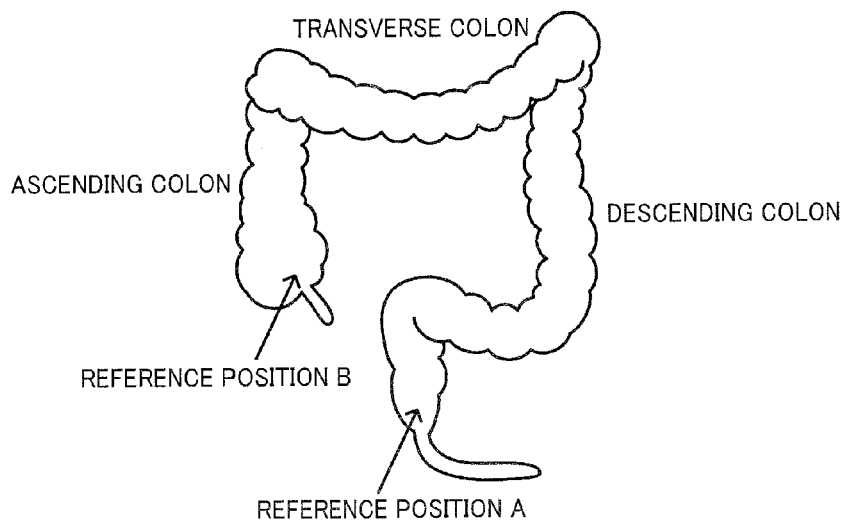
FIG. 13 is a view illustrative of the name of each region of a large intestine and a reference position.

The in vivo model acquisition section 343 acquires an in vivo model that schematically represents a tissue under control of the control section 350. The in vivo model acquisition section 343 includes a large-capacity hard disk drive, tape drive, or the like, and stores a plurality of site models. Note that the term "site model" used herein refers to a two-dimensional model that represents a site of a healthy subject (see FIG. 13 (large intestine model) for example). The in vivo model may be a three-dimensional model. The in vivo model may be acquired from the subject, or may be acquired from a different person. The in vivo model may be acquired from a different person each corresponding to each condition (e.g., physical feature (e.g., height and build) and sex). The in vivo model may be input to the image processing section 300 from a capsule endoscope apparatus, a CT apparatus, or an MRI apparatus via a network, and stored in the in vivo model acquisition section 343. The in vivo model is output to the on-model position determination section 342 and the linking section 344.

Figure 14:
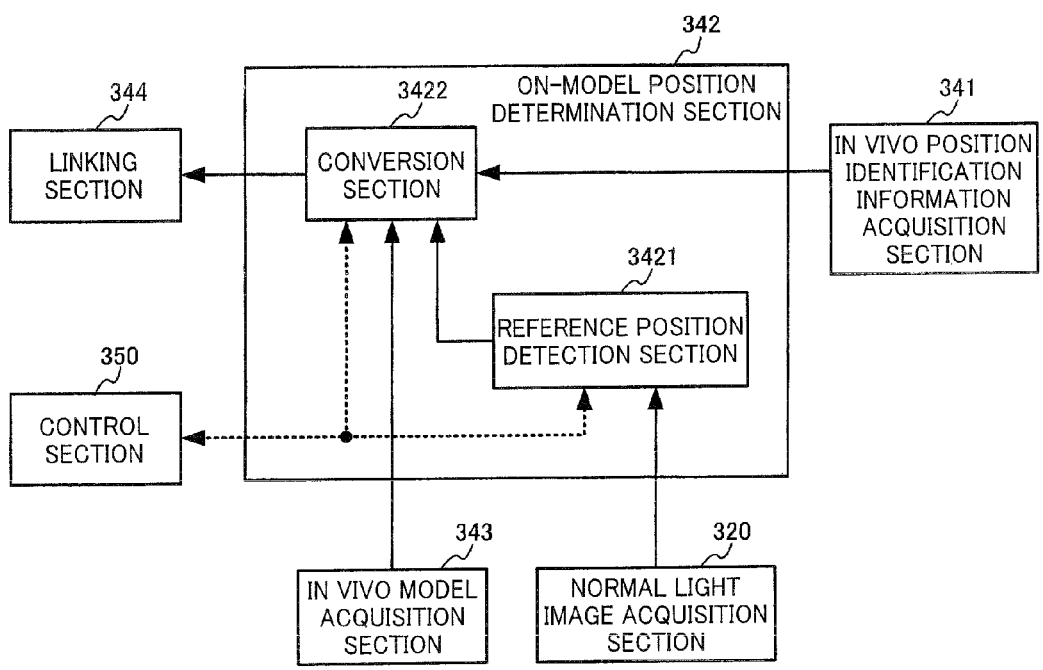
FIG. 14 shows a configuration example of an on-model position determination section.

The on-model position determination section 342 specifies an on-model position on the acquired site model corresponding to the calculated body imaging position under control of the control section 350. A specific configuration of the on-model position determination section 342 is described below. FIG. 14 is a block diagram illustrative of an example of the configuration of the on-model position determination section 342 according to the first embodiment. As shown in FIG. 14, the on-model position determination section 342 includes a reference position detection section 3421 and a conversion section 3422.

The reference position detection section 3421 detects a reference position (i.e., a reference position for the moving distance) under control of the control section 350. The measurement start point (i.e., reference position) refers to a start point where imaging using the endoscope apparatus has started. Specifically, the measurement start point is detected by calculating a feature point of the normal light image input from the normal light image acquisition section. In this case, the feature point is color information about the entire image. A point when the entire image is reddish indicates a start point where imaging using the endoscope apparatus has started. A reference position A shown in FIG. 13 corresponds to the measurement start point. Note that the reference position for the moving distance may be a start point where imaging of a given site using the endoscope apparatus has started. For example, a point where the in vivo position of the endoscope apparatus has changed from the large intestine to the small intestine may be set as the reference position. A reference position B shown in FIG. 13 corresponds to such a point. When the reference position detection section 3421 has detected the reference position, the reference position detection section 3421 outputs a detection signal to the conversion section 3422.

The conversion section 3422 converts the in vivo moving distance calculated by the in vivo position identification information acquisition section 341 into a distance on the in vivo model, and converts the in vivo moving direction into a moving direction on the in vivo model under control of the control section 350. The conversion section 3422 converts the calculated moving distance cL into a moving distance mL1 corresponding to the in vivo model scale by the following expression.

$$mL1 = modCoef \times cL \quad (4)$$

Note that modCoef is a coefficient based on the size of the in vivo model, and is set to each site model in advance.

When the imaging site is a target site of the shortening technique, the moving direction (h, v) is integrated from the reference position to calculate moving directions addH and addV. The on-model moving distance mL1 is corrected by the following expression using the moving direction to obtain a moving distance radL.

$$radL = mL1 \times \cos(addH) \times \cos(addV) \quad (5)$$

The moving distance radL corrected using the moving direction is integrated from the reference position to calculate a moving distance addL. The moving distance addL from the reference position is output to the linking section 344.

When the imaging site is not a target site of the shortening technique, a moving amount (x, y) on the in vivo model is calculated by the following expressions from the moving direction (h, v).

$$mL2 = modCoef \times L \quad (6)$$

$$(x, y) = (mL2 \times \sin(h) \times \cos(v), mL2 \times \cos(h) \times \cos(v)) \quad (7)$$

The moving amount (x, y) is integrated from the reference position to obtain a value (addX, addY). The value (addX, addY) indicates relative coordinates on the in vivo model from the reference position. The relative coordinates (addX, addY) from the reference position are output to the linking section 344.

FIGS. 15A and 15B show the process performed by the in vivo position identification information acquisition section 341 and the on-model position determination section 342. FIG. 15A shows the process performed when the endoscope apparatus moves through a curved tissue that has a curved section for which the shortening technique is used, and FIG. 15B shows the process performed when the shortening technique is not used.

The above process is described below with reference to FIGS. 15A and 15B. The moving distance information L and the moving direction information (h, v) are calculated from the image information. When using the shortening technique, the moving distance information L is corrected by the correction section 3413 (see FIG. 15A). Specifically, the moving distance information cL is calculated by multiplying the moving distance information L by the coefficient corCoef (see the expression (3)). The moving direction information (h, v) is not corrected.

The conversion section 3422 then performs the conversion process. Specifically, the moving distance information mL1 is calculated by multiplying the moving distance information cL by the coefficient modCoef (see the expression (4)). The moving direction information (h, v) is integrated from the reference position to calculate the integrated value (addH, addV). Since the moving direction information (h, v) indicates a change in angle per frame, the integrated value (addH, addV) indicates the current angle with respect to the reference position. The moving distance information radL is calculated from the moving distance information mL1 and the integrated value (addH, addV) (see the expression (5)).

Figure 16A:
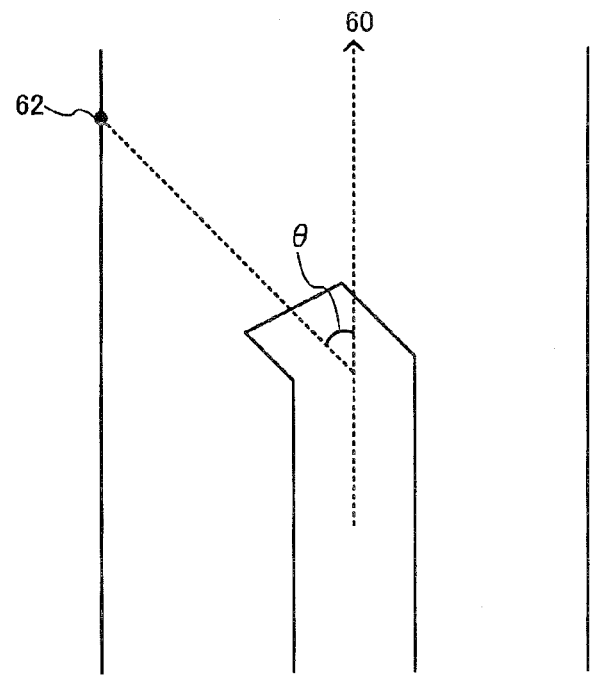
FIG. 16A is a view illustrative of the state of an endoscope apparatus when observing a lesion area in a hollow tubular site.
Figure 16B:
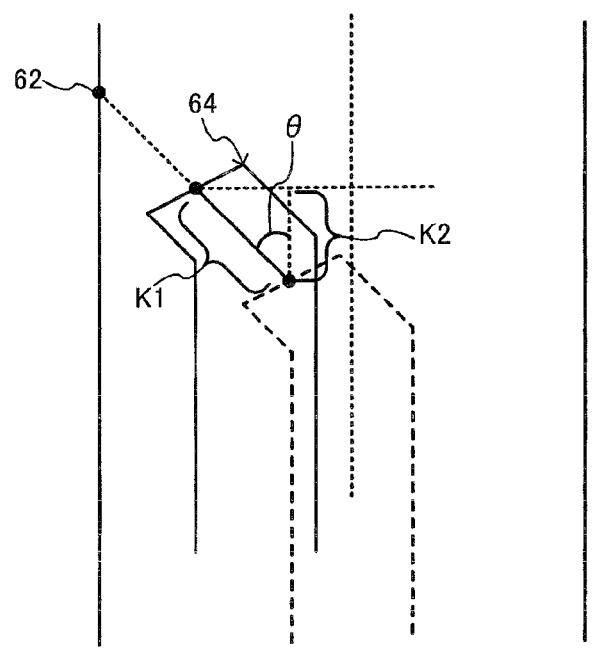
FIG. 16B is a view illustrative of the movement of an endoscope apparatus when observing a lesion area in detail.

The expression (5) is described below with reference to FIGS. 16A and 16B. FIG. 16A is a two-dimensional view showing the endoscope apparatus that moves through a hollow tubular site (e.g., large intestine). Note that the user can bend the end of the endoscope apparatus. In FIG. 16A, a lesion area 62 is observed in a state in which the end of the endoscope apparatus is bent by an angle θ with respect to a travel direction 60 (i.e., the moving direction at the reference position). The user is likely to move the endoscope apparatus to a position 64 shown in FIG. 16B in order to observe the lesion area in detail. In this case, the moving distance information obtained from the image information is a distance k1 shown in FIG. 16B. However, the moving distance in the travel direction 60 is k2. The moving distance k2 (k2=k1×cos θ) is necessary when specifying the on-model position. Therefore, the calculated moving distance is multiplied by cos(addH) and cos(addV) (see the expression (5)).

Although an example in which the user diagonally moves the endoscope apparatus in order to observe the lesion area in detail has been described above, a similar process is also performed when the endoscope apparatus has moved in the direction that perpendicularly intersects the travel direction 60, or the endoscope apparatus has diagonally moved during insertion or the like, for example.

The integrated value addL of the moving distance information radL from the reference position is calculated, and output to the linking section 344. In the above example, the distance information (i.e., one-dimensional information) is output when specifying the position on the two-dimensional site model (may be three-dimensional site model). A site for which the shortening technique is used is likely to be stretched along a straight line. If the endoscope apparatus moves through the site along a given path, the on-model position can be specified from the distance information.

The process performed when the shortening technique is not used is described below with reference to FIG. 15B. The moving distance information L and the moving direction information (h, v) are calculated from the image information in the same manner as in FIG. 15A.

The correction section 3413 does not perform the correction process. The conversion section 3422 calculates the moving distance information mL2 by multiplying the moving distance information L by the coefficient modCoef (see the expression (6)). The conversion section 3422 calculates the moving vector (x, y) from the moving distance information mL2 (on-model moving distance information) and the moving direction (h, v) (see the expression (7)). Since the moving vector (x, y) indicates the moving vector per frame, the desired coordinates (addX, addY) can be specified by integrating the moving vector (x, y) from the reference position.

The attention area detection section 345 is described below. The attention area detection section 345 detects an attention area from the acquired image under control of the control section 350. The term "focus area" used herein refers to an area of an in vivo (body) image that corresponds to a lesion area, for example. The attention area detection section 345 divides the acquired image into a plurality of areas, and calculates a feature quantity of each area. In this example, color information is used as the feature quantity. In a narrow-band image used as the special light image, a lesion area such as epidermoid cancer is drawn as a brown area. Therefore, the lesion area can be detected using the hue H as the feature quantity. The signal values of the R, G, and B channels are respectively referred to as r, g, and b, and indicated by 8 bits (0 to 255).

The hue H is calculated by the expressions (8) to (13) using the signal values r, g, and b, for example.

$$MAX=MAX(r,g,b) \quad (8)$$

The MAX function outputs the maximum argument among a plurality of arguments.

When MAX is 0:

$$H=0 \quad (9)$$

When MAX is not 0:

$$d=MAX(r,g,b)-MIN(r,g,b) \quad (10)$$

The MIN function outputs the minimum argument among a plurality of arguments.

When the signal value r is a maximum among the signal values r, g, and b:

$$H=60*(g-b)/d \quad (11)$$

When the signal value g is a maximum among the signal values r, g, and b:

$$H=60*\{2+(b-r)\}/d \quad (12)$$

When the signal value b is a maximum among the signal values r, g, and b:

$$H=60*\{4+(r-g)\}/d \quad (13)$$

When the hue H is smaller than 0, 360 is added to the hue H. The hue H is considered to be 0 when the hue H is 360.

The number of brown pixels included in each local area is used as the feature quantity of each local area. Note that the feature quantity of a lesion area is not limited to the above example. For example, the feature quantity of the color, the feature quantity of the spatial frequency, the feature quantity of the shape, the feature quantity of the area, and the like may be respectively calculated, multiplied by a weighting coefficient, and linearly combined to obtain the lesion feature quantity of each local area.

The attention area detection section 345 compares the feature quantity of each local area with a given threshold value, and determines whether or not each local area is the attention area based on the comparison result. In this case, a threshold value set in advance may be used, or the threshold value may be automatically set by the control section 350. The threshold value may be adaptively set based on the position within the special light image. A local area for which the feature quantity is equal to or larger than the threshold value is output to the linking section 344 as the attention area.

The linking section 344 links information about the acquired image to the specified on-model position under control of the control section 350. Note that the information about the acquired image is an indicator that indicates the position of the endoscope apparatus when the image has been acquired (i.e., when the in vivo site has been imaged). The linking section 344 links information about the attention area to the on-model position specified by the on-model position determination section 342. FIG. 17 shows an example of a guide image in which the position of the endoscope apparatus and the attention area are linked to the in vivo model. The guide image is output to the display section 400.

The display section 400 displays the normal light image output from the normal light image acquisition section 320 and the guide image output from the guide image generation section 340 at the same time. The display section 400 may display the image shown in FIG. 1, for example.

In this embodiment, each section of the image processing section 300 is implemented by hardware. Note that the configuration of the image processing section 300 is not limited thereto. For example, a CPU may perform the process of each section on an image acquired using the endoscope apparatus. Specifically, the process of each section may be implemented by means of software by causing the CPU to execute a program. Alternatively, part of the process of each section may be implemented by means of software.

When separately providing the imaging section, and implementing the process of each section of the image processing section 300 by means of software, a known computer system (e.g., work station or personal computer) may be used as the image processing device. A program (image processing program) that implements the process of each section of the image processing section 300 may be provided in advance, and executed by the CPU of the computer system.

Figure 18:
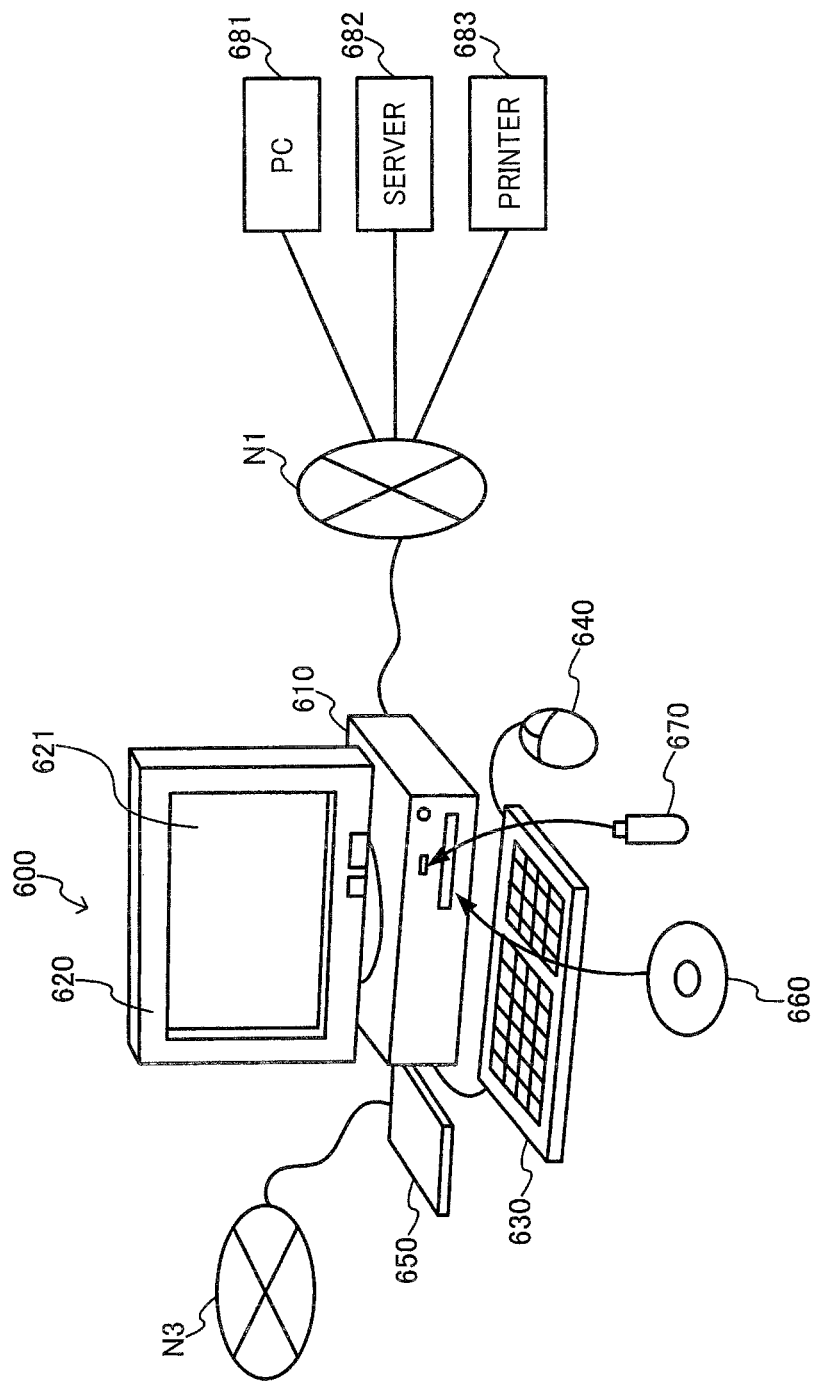
FIG. 18 shows a configuration example of a computer used for a software process.
Figure 19:
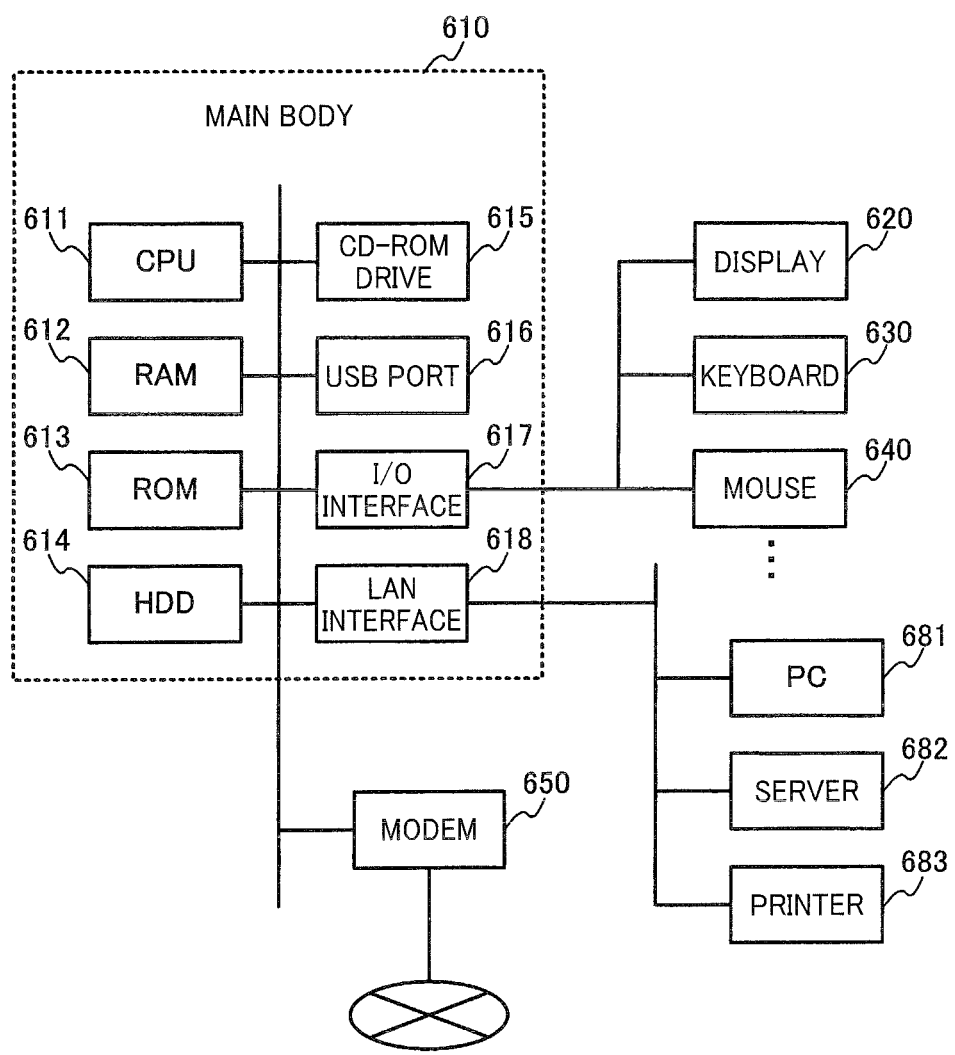
FIG. 19 shows a configuration example of a computer used for a software process.

FIG. 18 is a system configuration diagram showing the configuration of a computer system 600 according to this modification. FIG. 19 is a block diagram showing the configuration of a main body 610 of the computer system 600. As shown in FIG. 18, the computer system 600 includes the main body 610, a display 620 that displays information (e.g., image) on a display screen 621 based on instructions from the main body 610, a keyboard 630 that allows the user to input information to the computer system 600, and a mouse 640 that allows the user to designate an arbitrary position on the display screen 621 of the display 620.

As shown in FIG. 19, the main body 610 of the computer system 600 includes a CPU 611, a RAM 612, a ROM 613, a hard disk drive (HDD) 614, a CD-ROM drive 615 that receives a CD-ROM 660, a USB port 616 to which a USB memory 670 is removably connected, an I/O interface 617 that connects the display 620, the keyboard 630, and the mouse 640, and a LAN interface 618 that is used to connect to a local area network or a wide area network (LAN/WAN) N1.

The computer system 600 is connected to a modem 650 that is used to connect to a public line N3 (e.g., Internet). The computer system 600 is also connected to personal computer (PC) 681 (i.e., another computer system), a server 682, a printer 683, and the like via the LAN interface 618 and the local area network or the large area network N1.

Figure 21:
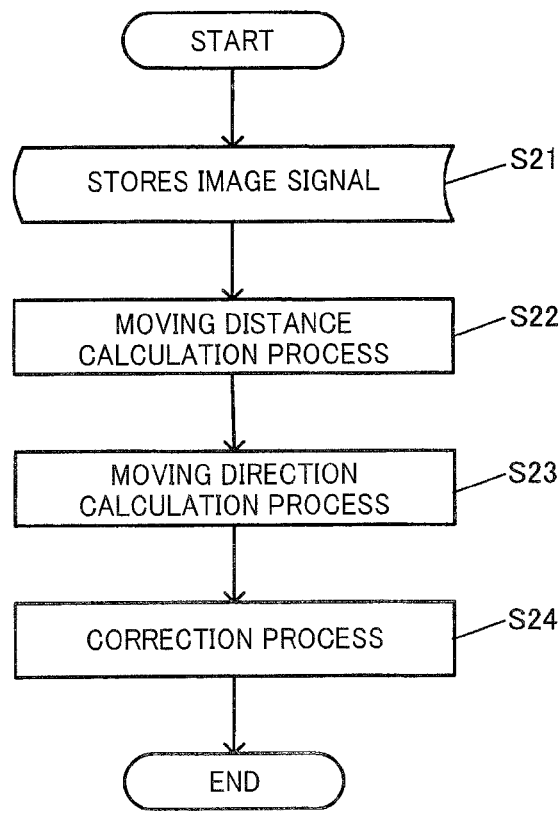
FIG. 21 is a flowchart illustrative of an in vivo position identification information acquisition process.
Figure 22:
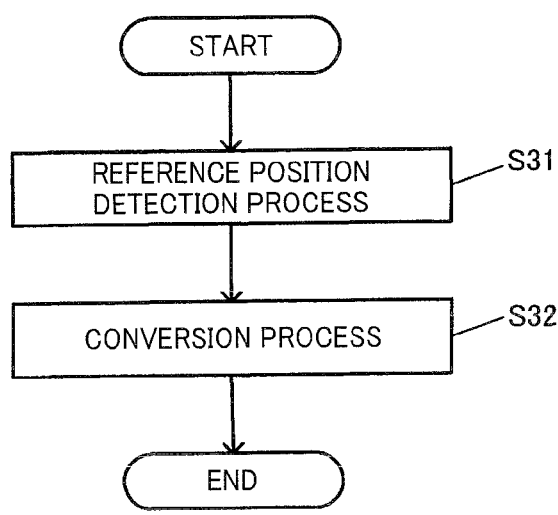
FIG. 22 is a flowchart illustrative of an on-model position determination process.

The computer system 600 implements the functions of the image processing device by reading an image processing program (e.g., an image processing program that implements a process described later referring to FIGS. 20 to 22) recorded on a given recording medium, and executing the image processing program. The given recording medium may be an arbitrary recording medium that records the image processing program that can be read by the computer system 600, such as the CD-ROM 660, the USB memory 670, a portable physical medium (e.g., MO disk, DVD disk, flexible disk (FD), magnetooptical disk, or IC card), a stationary physical medium (e.g., HDD 614, RAM 612, or ROM 613) that is provided inside or outside the computer system 600, or a communication medium that temporarily stores a program during transmission (e.g., the public line N3 connected via the modem 650, or the local area network or the wide area network N1 to which the computer system (PC) 681 or the server 682 is connected).

Specifically, the image processing program is recorded on a recording medium (e.g., portable physical medium, stationary physical medium, or communication medium) so that the image processing program can be read by a computer. The computer system 600 implements the functions of the image processing device by reading the image processing program from such a recording medium, and executing the image processing program. Note that the image processing program need not necessarily be executed by the computer system 600. The invention may be similarly applied to the case where the computer system (PC) 681 or the server 682 executes the image processing program, or the computer system (PC) 681 and the server 682 execute the image processing program in cooperation.

A process performed when implementing the process of the guide image generation section 340 shown in FIG. 9 on the normal light image and the special light image acquired in advance by means of software is described below using a flowchart shown in FIG. 20 as an example of implementing part of the process of each section by means of software.

Header information (e.g., observation target, photographing mode, and illumination light synchronization signal) is input to the time-series normal light image and the special light image (S11). An in vivo model corresponding to the observation target is input from the header information (S12). The special light image and the normal light image are input to an image buffer provided in advance (S13). The in vivo position identification information that specifies the in vivo position of the endoscope apparatus when the image has been acquired (i.e., when the in vivo site has been imaged), is acquired from the normal light image based on the moving distance of the endoscope apparatus and the in vivo moving direction of the endoscope apparatus (described in detail later with reference to FIG. 21) (S14). The on-model position on the input site model is specified based on the acquired in vivo position identification information (described in detail later with reference to FIG. 22) (S15). A focus candidate area is detected from the special light image (S16). The information about the input image is then linked to the specified on-model position (S17). The information about the acquired image is an indicator that indicates the position of the endoscope apparatus when the image has been acquired (i.e., when the in vivo site has been imaged). A guide image in which the indicator that indicates the position of the endoscope apparatus when the image has been acquired (i.e., when the in vivo site has been imaged) is linked to the on-model position is then output (S18). Whether or not the process has been performed on the final time-series image is determined (S19). When it has been determined that the process has not been performed on the final image, the above process is performed on the next image signal from the step S13. When it has been determined that the process has been performed on all of the image signals, the process is terminated.

Figure 20:
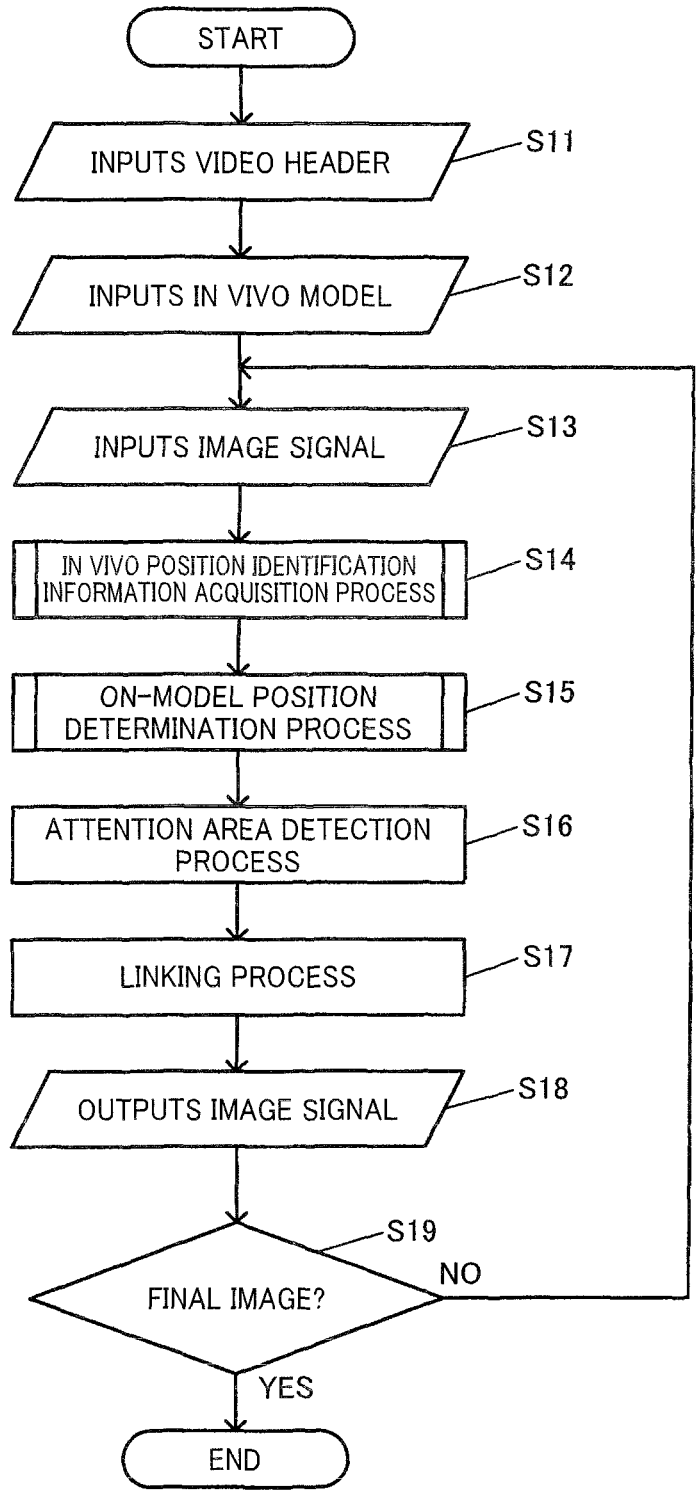
FIG. 20 is a flowchart illustrative of a process according to one embodiment of the invention.

The details of the in vivo position identification information acquisition process performed in the step S14 shown in FIG. 20 are described below with reference to FIG. 21.

The image signal of the normal light image is stored (S21). A feature point of the input image signal is matched with a feature point of the image signal input in the preceding frame, and the in vivo moving distance of the endoscope apparatus is calculated based on the matching result (S22). A feature point of the input image signal is matched with a feature point of the image signal input in the preceding frame, and the in vivo moving direction of the endoscope apparatus is calculated based on the matching result (S23). The in vivo moving distance of the endoscope apparatus thus calculated is corrected based on the structural properties of the entirety or part of the tissue where the endoscope apparatus has moved (S24).

The details of the on-model position determination process performed in the step S15 shown in FIG. 20 are described below with reference to FIG. 22.

A reference position (i.e., measurement start point) for the moving distance is detected (S31). The in vivo moving distance and the in vivo moving direction of the endoscope apparatus calculated by the in vivo position identification information acquisition process are, converted into a distance and a direction on the in vivo model (S32).

This makes it possible to examine the subject while visually determining the site of the body that corresponds to the acquired image using the guide image, so that the burden imposed on the operator can be reduced.

Since the in vivo model and the actual in vivo position of the endoscope apparatus can be displayed while performing the correction process, the site that corresponds to the acquired image can be determined with high accuracy.

Moreover, the endoscope apparatus can be easily moved to the attention area when observing the attention area again by linking the attention area detected using the special light image to the guide image.

Figure 3:
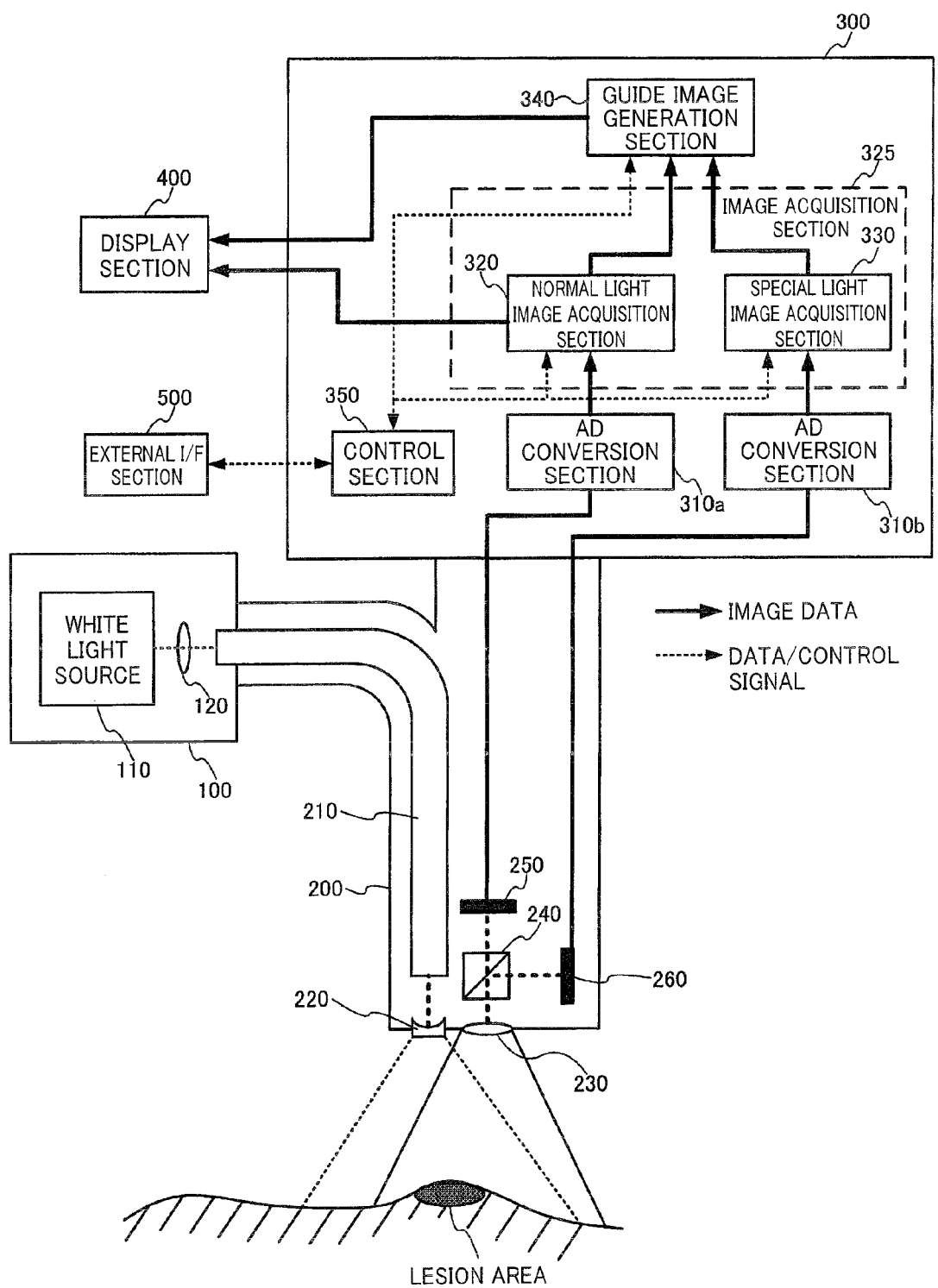
FIG. 3 shows a system configuration example according to one embodiment of the invention.

According to the first embodiment, the image acquisition section 325 of the image processing device shown in FIG. 3 acquires an image that has been acquired by imaging an arbitrary site inside the subject using the endoscope apparatus. The in vivo position identification information acquisition section 341 shown in FIG. 9 acquires information that specifies the in vivo position of the endoscope apparatus when the image has been acquired (i.e., when the in vivo site has been imaged), based on the acquired image. The in vivo model acquisition section 343 acquires the in vivo model that is a model of the site of the subject. The on-model position determination section 342 specifies the on-model position on the acquired site model corresponding to the in vivo position identification information, and the linking section 344 links information about the acquired image to the specified on-model position.

Specifically, the image and the in vivo position identification information are acquired, the on-model position is specified based on the in vivo position identification information, and the information about the acquired image is linked to the specified on-model position, so that the in vivo position of the endoscope apparatus can be detected. An image processing device that supports diagnosis and an operation by the operator can be provided by displaying the guide image to which the in vivo position of the endoscope apparatus is linked. Specifically, the image shown in FIG. 1 may be displayed.

The in vivo position identification information acquisition section 341 acquires the in vivo position identification information based on the image acquired by the image acquisition section 325.

Specifically, since the position can be detected based on image processing, an extensive apparatus is unnecessary as a means that detects the in vivo position of the endoscope apparatus.

As shown in FIG. 10, the in vivo position identification information acquisition section 341 includes the distance information calculation section 3412 that calculates the moving distance information that indicates the moving distance of the endoscope apparatus. The in vivo position identification information acquisition section 341 acquires the calculated moving distance information as in vivo position identification information.

This makes it possible to acquire the moving distance information as the in vivo position identification information. Therefore, the position can be detected based on the moving distance.

The in vivo position identification information acquisition section 341 includes the direction information calculation section 3411 that calculates the moving direction information that indicates the moving direction of the endoscope apparatus. The in vivo position identification information acquisition section 341 acquires the calculated moving direction information as in vivo position identification information.

This makes it possible to acquire the moving direction information as the in vivo position identification information. Therefore, the position can be detected based on the moving direction. Moreover, it is possible to perform a different process on the moving distance and the moving direction.

The image acquisition section 325 acquires a first image at a first timing, and acquires a second image at a second timing that occurs after the first timing. The in vivo position identification information may be acquired based on the result of the matching process on the first image and the second image.

This makes it possible to calculate the in vivo position identification information by the matching process on two images (see FIGS. 11A and 11B). Therefore, the position can be detected without using an extensive apparatus. Moreover, the moving distance of the endoscope apparatus can be successively calculated at short intervals (e.g., 1/30th of a second or 1/60th of a second). Note that the in vivo position identification information may be acquired based on a monocular acquired image by providing a zoom mechanism or a beam emitting mechanism, and performing three-dimensional measurement using the functions of the zoom mechanism or the beam emitting mechanism.

As shown in FIG. 10, the in vivo position identification information acquisition section 341 includes the correction section 3413 that corrects the moving distance information calculated by the distance information calculation section 3412 based on the structural properties of the entirety or part of the tissue where the endoscope apparatus has moved. The on-model position determination section 342 specifies the on-model position based on the moving distance information corrected by the correction section 3413.

The correction section 3413 performs the correction process that increases the moving distance (distance indicated by the moving distance information) when the endoscope apparatus has moved through a curved tissue that has a curved section, for example. The curved tissue may be a large intestine or a small intestine.

This makes it possible to correct the difference between the moving distance on the guide image and the in vivo moving distance of the endoscope apparatus based on the structural properties of the site. This applies to a case of using the shortening technique. The shortening technique facilitates insertion of the endoscope apparatus by linearly extending the curved tissue that has a curved section (see FIGS. 2A and 2B). Therefore, it is considered that the on-model position has advanced through the site as compared with the distance information calculated by the distance information calculation section. Accordingly, the correction section 3413 increases the moving distance. Specific examples of the curved tissue that has a curved section include a descending colon shown in FIG. 13, and the like.

As shown in FIG. 14, the on-model position determination section 342 includes the conversion section 3422 that converts the moving distance information corrected by the correction section 3413 into an on-model distance. The on-model position determination section 342 specifies the on-model position based on the on-model distance obtained by the conversion section 3422.

This makes it possible to appropriately specify the on-model position irrespective of the size of the in vivo model (e.g., 500×500 pixels or 1000×1000 pixels).

As shown in FIG. 14, the on-model position determination section 342 includes the reference position detection section 3421 that detects the reference position that indicates the start point of the movement of the endoscope apparatus. The on-model position determination section 342 specifies a position distant from the reference position by the on-model distance (distance obtained by the conversion section 3422) as the on-model position.

This makes it possible to specify the on-model position based on the reference position. Therefore, even if the position of the endoscope apparatus on the guide image differs from the in vivo position of the endoscope apparatus, accumulation of such a difference can be suppressed by resetting the reference position, so that an appropriate on-model position can be specified.

The in vivo position identification information acquisition section 341 includes the direction information calculation section 3411, and the conversion section 3422 converts the moving direction information calculated by the direction information calculation section 3411 into an on-model direction. The on-model position determination section 342 specifies a position that is distant from the reference position by the on-model distance in the on-model direction as the on-model position.

This makes it possible to specify the on-model position based on the reference position, the moving distance information, and the moving direction information. It is also possible to specify the on-model position even if the angle of the in vivo model has changed.

The on-model position determination section 342 includes the reference position detection section 3421, and may specify the on-model position based on the reference position and the in vivo position identification information.

The reference position may be the measurement start point where imaging using the endoscope apparatus has started (e.g., anus (i.e., insertion point)), or a point where imaging of a given site using the endoscope apparatus has started (e.g., a transition point from the descending colon to the transverse colon), for example.

This makes it possible to specify the on-model position based on the reference position and the in vivo position identification information. The reference position may be the reference position A or the reference position B shown in FIG. 13, for example. Accumulation of a difference between the position of the endoscope apparatus on the guide image and the in vivo position of the endoscope apparatus can be suppressed by setting the reference position, so that an appropriate on-model position can be specified.

The image processing device according to this embodiment includes the attention area detection section 345 that detects the attention area from the acquired image. The linking section 344 shown in FIG. 9 links information about the attention area in the attention image (i.e., an acquired image that includes the attention area) to the on-model position specified by the on-model position determination section 342.

The attention area is a lesion area, for example. The attention area detection section 345 detects the attention area based on the special light image that includes an object image including information in a wavelength band narrower than that of white light.

This makes it possible to detect the attention area from the acquired image, and link information about the attention image to the on-model position. Therefore, the information about the image including the lesion area can be linked to the position of the lesion area (see FIG. 17), so that the in vivo position of the lesion area can be visually and easily determined. The ratio of brown increases in the lesion area (e.g., epidermoid cancer) by utilizing the special light image, so that the focus are can be easily determined.

The linking section 345 may link an indicator that indicates the position of the endoscope apparatus when the image has been acquired (i.e., when the in vivo site has been imaged) as the information about the acquired image.

In this case, since the guide image can be displayed while linking the acquired image to the guide image, the operator can easily determine the site that corresponds to the acquired image.

An image processing method according to this embodiment may include acquiring an image that has been acquired by imaging a tissue using an endoscope apparatus, acquiring in vivo position identification information that specifies an in vivo position when the image has been acquired, acquiring an in vivo model that is a model of the tissue, specifying an on-model position that corresponds to the position specified by the in vivo position identification information on the acquired site model, and linking information about the acquired image to the specified on-model position.

This makes it possible to detect the in vivo position of the endoscope apparatus, and support diagnosis and operation of the operator by displaying the guide image to which the in vivo position of the endoscope apparatus is linked.

The image acquisition section 325 shown in FIG. 3 acquires a first image (i.e., normal light image) and a second image (i.e., special light image). The first image and the second image are in vivo images. A specific wavelength band included in the in vivo image is a wavelength band absorbed by hemoglobin in blood. The wavelength absorbed by hemoglobin is 390 to 445 nm (i.e., component B2 of narrow-band light) or 530 to 550 nm (i.e., component G2 of narrow-band light), for example.

This makes it possible to implement narrow-band observation referred to as narrow-band imaging (NBI), so that the structure of a surface area of a tissue and a vessel located in a deep area can be observed. A lesion area (e.g., epidermoid cancer) that cannot be easily observed using normal light can be displayed as a brown area or the like in light by inputting the resulting signal to a given channel (G2→R, B2→G and B), so that the lesion area can be reliably detected. A wavelength of 390 to 445 nm or 530 to 550 nm is selected from the viewpoint of absorption by hemoglobin and the ability to reach a surface area or a deep area of a tissue. Note that the wavelength band is not limited thereto. For example, the lower limit of the wavelength band may decrease by about 0 to 10%, and the upper limit of the wavelength band may increase by about 0 to 10% depending on a variation factor (e.g., experimental results for absorption by hemoglobin and the ability of reaching a surface area or a deep area of a tissue).

The specific wavelength band included in the in vivo image may be the wavelength band of fluorescence emitted from a fluorescent substance. For example, the specific wavelength band may be 490 to 625 nm.

This enables autofluorescence imaging (AFI). Intrinsic fluorescence (490 to 625 nm) from a fluorescent substance (e.g., collagen) can be observed by applying excitation light (390 to 470 nm). In this case, the lesion area can be highlighted in a color differing from that of a normal mucous membrane, so that the lesion area can be reliably detected, for example. A wavelength band of 490 to 625 nm is the wavelength band of fluorescence emitted from a fluorescent substance (e.g., collagen) when excitation light is applied. A wavelength band of 390 to 470 nm is the wavelength band of excitation light that causes fluorescence to occur.

Note that the wavelength band is not limited thereto. For example, the lower limit of the wavelength band may decrease by about 0 to 10%, and the upper limit of the wavelength band may increase by about 0 to 10% depending on a variation factor (e.g., experimental results for the wavelength band of fluorescence emitted from a fluorescent substance). A pseudocolor image may be generated by applying light within a wavelength band of 540 to 560 nm that is absorbed by hemoglobin.

The specific wavelength band included in the in vivo image may be an infrared wavelength band. For example, the specific wavelength band may be 790 to 820 nm or 905 to 970 nm.

This enables infrared imaging (IRI). Information about the vessel or the blood flow in a deep area of the mucous membrane that cannot be easily observed visually can be highlighted by intravenously injecting indocyanine green (ICG) (infrared marker) that easily absorbs infrared light, and applying infrared light within the above wavelength band, so that the depth of cancer invasion or the therapeutic strategy can be determined, for example. An infrared marker exhibits maximum absorption in a wavelength band of 790 to 820 nm, and exhibits minimum absorption in a wavelength band of 905 to 970 nm Note that the wavelength band is not limited thereto. For example, the lower limit of the wavelength band may decrease by about 0 to 10%, and the upper limit of the wavelength band may increase by about 0 to 10% depending on a variation factor (e.g., experimental results for absorption of the infrared marker).

An example in which the image acquisition section 325 includes the normal light image acquisition section 320 and the special light image acquisition section 330, and the image acquisition section 325 acquires the first image (normal light image) and the second image (special light image) has been described above. Note that another configuration may be employed. For example, the special light image may be used to detect the lesion position and displayed on the display section 400, or the normal light image may be used to detect the lesion position and displayed on the display section 400.

A program according to this embodiment causes a computer to function as the image acquisition section 325, the in vivo position identification information acquisition section 341, the in vivo model acquisition section 343, the on-model position determination section 342, and the linking section 345. The image acquisition section 325 acquires an image obtained by imaging a site using an endoscope apparatus, and the in vivo position identification information acquisition section 341 acquires in vivo position identification information that specifies the in vivo position of the endoscope apparatus when the site has been imaged. The in vivo model acquisition section 343 acquires an in vivo model, and the on-model position determination section 342 specifies an on-model position that corresponds to the position specified by the in vivo position identification information. The linking section 345 links information about the acquired image to the specified on-model position.

This makes it possible to store image data, and process the stored image data by means of software using a computer system (e.g., PC) (e.g., capsule endoscope).

A computer program product according to this embodiment stores a program code that implements each section (image acquisition section, in vivo position identification information acquisition section, site model acquisition section, on-model position determination section, and linking section) according to this embodiment.

The program code implements an image acquisition section that acquires an image that has been acquired by imaging a tissue using an endoscope apparatus, an in vivo position identification information acquisition section that acquires in vivo position identification information that specifies an in vivo position of the endoscope apparatus when the image has been acquired, an in vivo model acquisition section that acquires an in vivo model that is a model of the tissue, an on-model position determination section that specifies an on-model position that corresponds to the position specified by the in vivo position identification information on the acquired site model, and a linking section that links information about the acquired image to the specified on-model position.

The term "computer program product" used herein refers to an information storage medium, a device, an instrument, a system, or the like that stores a program code, such as an information storage medium (e.g., optical disk medium (e.g., DVD), hard disk medium, and memory medium) that stores a program code, a computer that stores a program code, or an Internet system (e.g., a system including a server and a client terminal), for example. In this case, each element and each process according to this embodiment are implemented by corresponding modules, and a program code that includes the modules is recorded (stored) in the computer program product.

3. Second Embodiment

Figure 23:
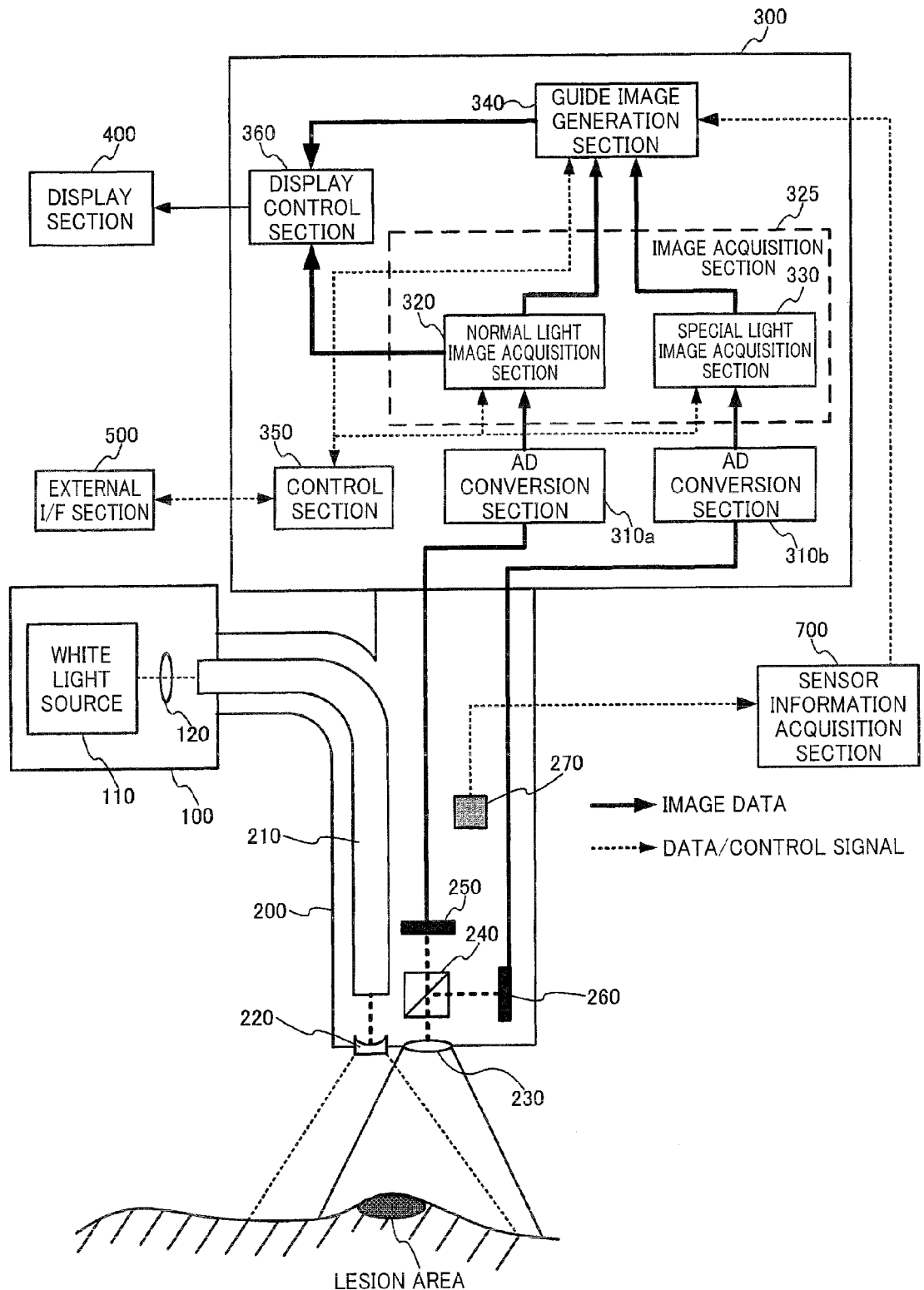
FIG. 23 shows another system configuration example according to one embodiment of the invention.

An endoscope apparatus that includes an image processing device according to a second embodiment of the invention is described below. FIG. 23 shows the endoscope apparatus according to the second embodiment. The endoscope apparatus according to the second embodiment includes a sensor 270, a sensor information acquisition block (sensor information acquisition section 700), and a display control section 360 in addition to the elements of the endoscope apparatus according to the first embodiment. The endoscope apparatus according to the second embodiment also differs from the endoscope apparatus according to the first embodiment as to the configuration of the in vivo position identification information acquisition section.

The sensor 270 is a triaxial acceleration sensor or the like. For example, the sensor 270 measures accelerations along x, y, and z axes, and transmits information about the measured accelerations (acceleration information) to the sensor information acquisition section 700. The sensor information acquisition section 700 acquires movement information from the acquired acceleration information, and transmits the movement information to the guide image generation section 340.

The movement information may be acceleration information, or velocity information obtained by integrating the acceleration information. The movement information may be a three-dimensional moving path obtained by integrating the velocity information.

Figure 24:
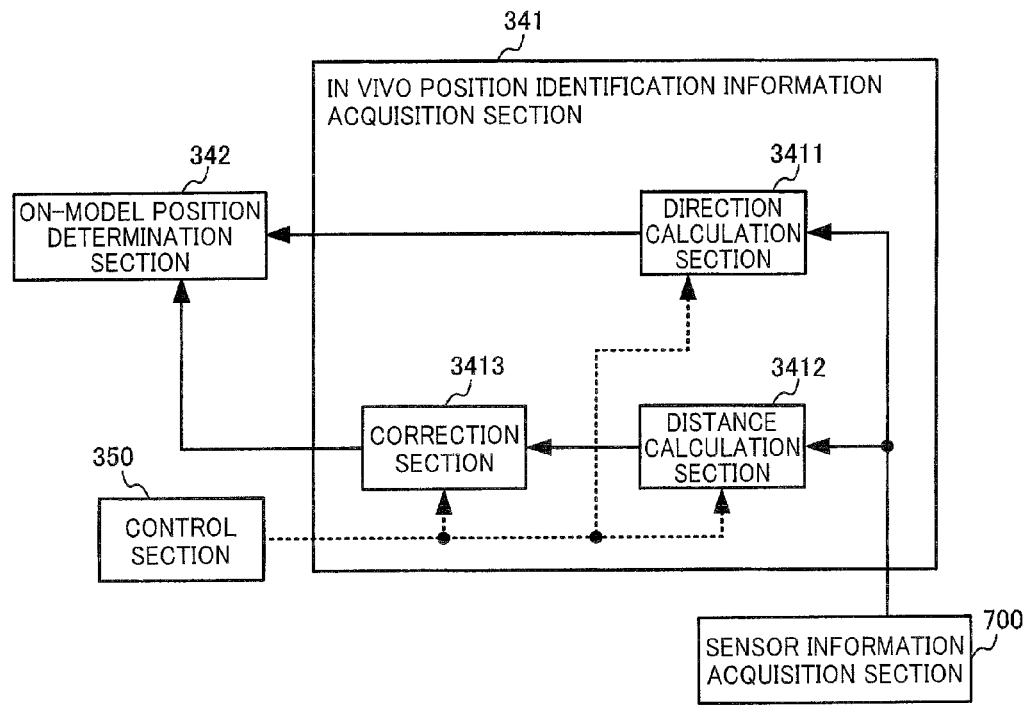
FIG. 24 shows another configuration example of an in vivo position identification information acquisition section.

The guide image generation section 340 includes the in vivo position identification information acquisition section 341 in the same manner as in the first embodiment. FIG. 24 shows the configuration of the in vivo position identification information acquisition section 341 according to this embodiment. The in vivo position identification information acquisition section 341 according to this embodiment differs from the in vivo position identification information acquisition section 341 according to the first embodiment in that the image storage section 3410 is omitted. The in vivo position identification information acquisition section 341 according to this embodiment receives the sensor information (movement information) from the sensor information acquisition section 700 instead of the normal light image from the normal light image acquisition section 320.

The distance calculation section 3412 calculates the moving distance information based on the movement information from the sensor information acquisition section 700, and the direction calculation section 3411 calculates the moving direction information based on the movement information from the sensor information acquisition section 700. The process performed after the moving distance information L and the moving direction information (h, v) have been obtained is the same as that of the first embodiment. Specifically, the correction section 3413 performs the correction process (correction of a difference due to the shortening technique), and the conversion section 3422 of the on-model position determination section 342 coverts the moving direction information into an on-model distance. An on-model position is then specified.

According to this embodiment, the image processing device includes the sensor information acquisition section 700 that acquires the sensor information from the sensor 270. The image processing device acquires the movement information about the endoscope apparatus as the in vivo position identification information based on the sensor information.

This makes it possible to acquire the in vivo position identification information based on the sensor information. When the sensor 270 is a triaxial acceleration sensor that measures accelerations along x, y, and z axes (velocity or displacement when integrating the accelerations), direct and accurate data can be acquired as compared with image processing. When using an ultrasonic sensor or the like, an absolute position can be calculated instead of a relative position.

The image processing device includes the display control section 360 that controls display of the in vivo model image (guide image) and the acquired image. The display control section 360 may deform the in vivo model image based on the movement information.

Figure 2B:
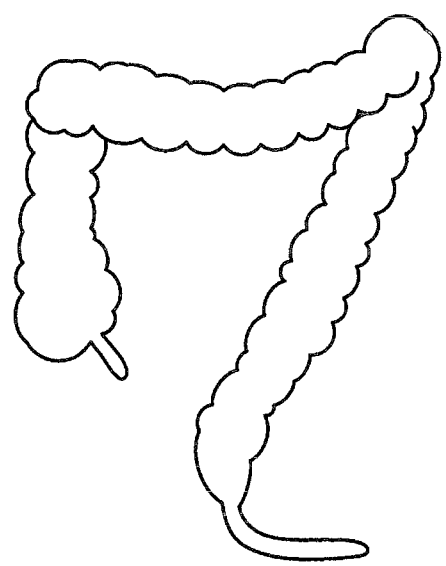
FIG. 2B is a view showing state of a large intestine when using a shortening technique.

For example, when it has been determined that the curved tissue is linearly extended (see FIG. 2B) based on the sensor information (movement information), the display control section 360 deforms the in vivo model image as shown in FIG. 2B.

This makes it possible to display the in vivo model image that has a shape similar to the shape of the in vivo site during imaging (during insertion of the endoscope apparatus), so that the user (doctor) can make a diagnosis or the like while watching an image that coincides with the maneuvering feeling of the endoscope apparatus. The above method is considered to be more effective when used together with a sensor (e.g., ultrasonic sensor) that calculates an accurate absolute position.

4. Third Embodiment

An endoscope apparatus that includes an image processing device according to a third embodiment is described below. The image processing device according to the third embodiment differs from the image processing device according to the first embodiment as to the in vivo position identification information acquisition section 341 and the on-model position determination section 342.

Figure 25:
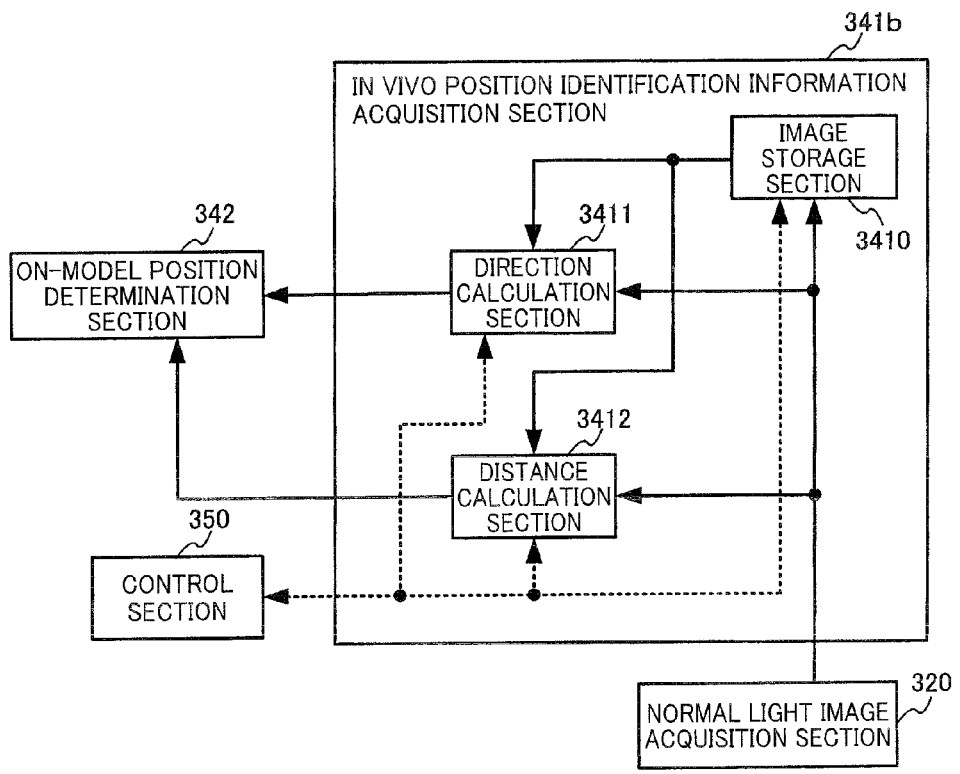
FIG. 25 shows yet another configuration example of an in vivo position identification information acquisition section.

FIG. 25 shows an in vivo position identification information acquisition section 341b according to this embodiment. The in vivo position identification information acquisition section 341b differs from the in vivo position identification information acquisition section 341 in that the correction section 3413 is omitted. The moving distance L calculated by the distance calculation section 3412 is output to the on-model position calculation section.

Figure 26:
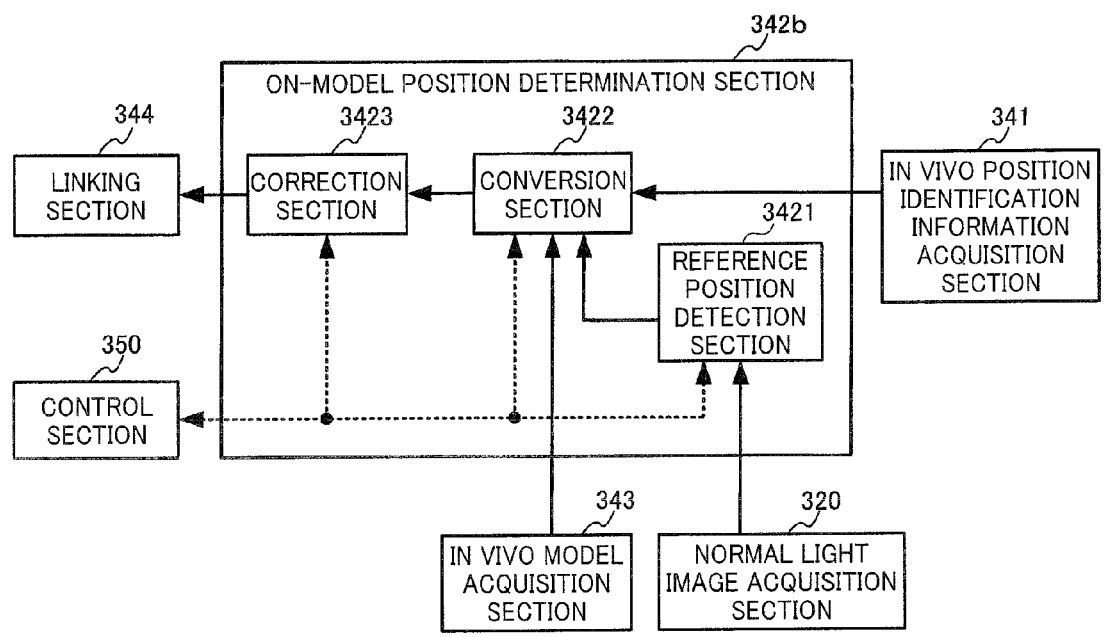
FIG. 26 shows another configuration example of an on-model position determination section.

FIG. 26 shows an on-model position determination section 342b according to this embodiment. The on-model position determination section 342b differs from the on-model position determination section 342 in that the on-model position determination section 342b further includes a correction section 3423.

The correction section 3423 corrects the moving distance on the in vivo model based on the structural properties of the entirety or part of the tissue where the endoscope apparatus has moved under control of the control section 350. Specifically, the correction section 3423 increases, the moving distance within the entirety or part of a curved tissue into which the endoscope apparatus is inserted using the shortening technique. Specifically, since the shortening technique shortens the intestine by folding the intestine, the moving distance on the in vivo model is longer than the calculated moving distance. A corrected moving distance cmL is calculated by the following expressions.

$$mL = modCoed \times L \tag{14}$$

$$radL = mL \times \cos(addH) \times \cos(addV) \tag{15}$$

$$cmL = corModCoef \times radL \tag{16}$$

Note that corModCoef is a coefficient having a value of 1 or more. The coefficient corModCoef may be determined by the operator in advance, or may be automatically calculated by the control section 350 based on patient information.

When the imaging site is not a target site of the shortening technique, a moving amount (x, y) on the in vivo model is calculated by the following expressions from the moving direction (h, v).

$$mL = modCoef \times L \tag{17}$$

$$(x,y) = (mL \times \sin(h) \times \cos(v), mL \times \cos(h) \times \cos(v)) \tag{18}$$

The moving amount (x, y) is integrated from the reference position to obtain a value (addX, addY). The value (addX, addY) indicates relative coordinates on the in vivo model from the reference position. The relative coordinates (addX, addY) from the reference position are output to the linking section 344.

Figure 27A:
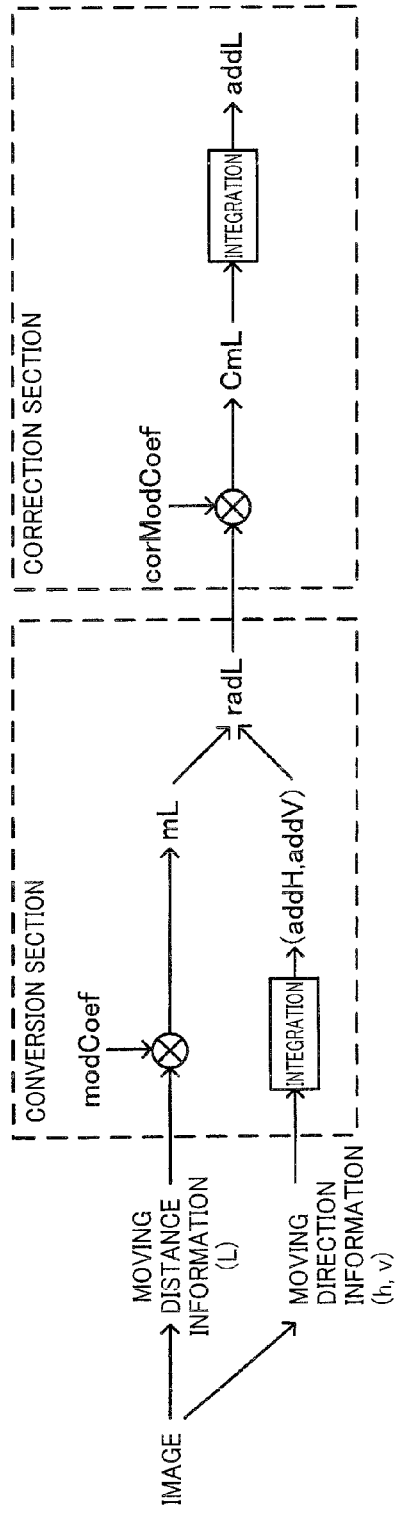
FIG. 27A is a view illustrative of a conversion process and a correction process when using a shortening technique.
Figure 27B:
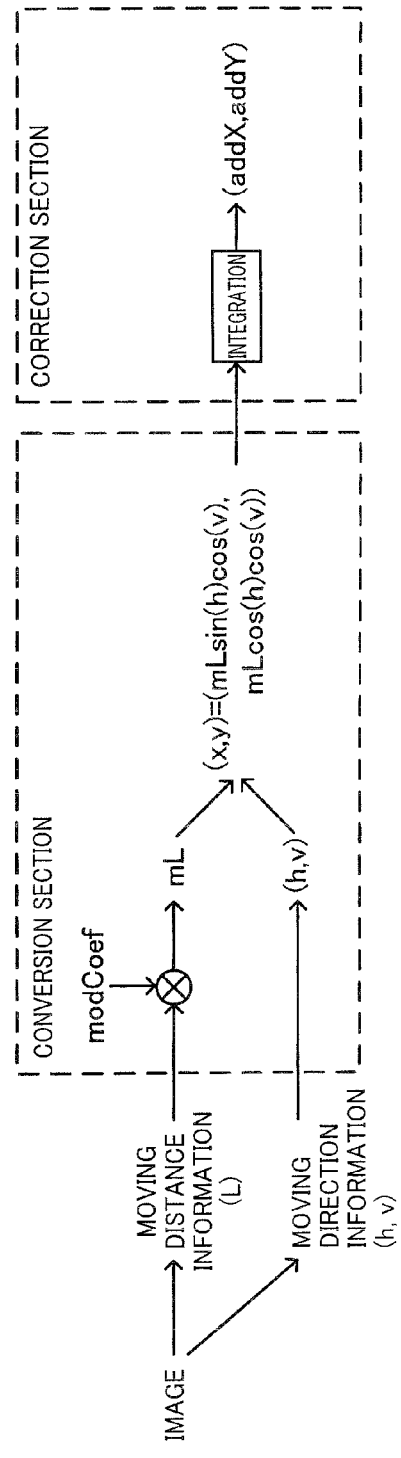
FIG. 27B is a view illustrative of a conversion process and a correction process when a shortening technique is not used.

FIGS. 27A and 27B shows the above process. FIG. 27A shows the process performed when the endoscope apparatus moves through a curved tissue for which the shortening technique is used, and FIG. 27B shows the process performed when the shortening technique is not used.

The above process is described below with reference to FIGS. 27A and 27B. The moving distance information L and the moving direction information (h, v) are calculated from the image information. When using the shortening technique, the moving distance information L is corrected by the correction section 3423 (see FIG. 27A). Specifically, the moving distance information mL is calculated by multiplying the moving distance information L by the coefficient modCoef, the direction is corrected using the integrated value (addH, addV), and the moving distance information radL is calculated (see the expressions (14) and (15)).

The correction section 3413 then performs the correction process. Specifically, the moving distance information cmL is calculated by multiplying the moving distance information radL by the coefficient corModCoef (see the expression (16)). The integrated value addL is calculated by integrating the moving distance information cmL, and output to the linking section 344.

The process performed when the shortening technique is not used is described below with reference to FIG. 27B. The moving distance information L and the moving direction information (h, v) are calculated from the image information in the same manner as in FIG. 27A.

As shown in FIG. 27B, the conversion section 3422 performs the conversion process. Specifically, the moving distance information mL is calculated by multiplying the moving distance information L by the coefficient modCoef, and the moving vector (x,y) is calculated from the moving distance information mL (on-model moving distance information) and the moving direction (h, v) (see the expressions (17) and (18)). Since the moving vector (x, y) indicates the moving vector per frame, the desired coordinates (addX, addY) can be specified by integrating the moving vector (x, y) from the reference position.

According to this embodiment, the on-model position determination section 342 includes the conversion section 3422 that converts the distance indicated by the moving distance information into the on-model distance (i.e., distance on the in vivo model), as shown in FIG. 26. The on-model position determination section 342 specifies the on-model position based on the on-model distance obtained by the conversion section 3422.

This makes it possible to appropriately specify the on-model position irrespective of the size of the in vivo model.

As shown in FIG. 26, the on-model position determination section 342 includes the correction section 3423 that corrects the on-model distance obtained by the conversion section 3422 based on the structural properties of the entirety or part of the tissue where the endoscope apparatus has moved. The on-model position determination section 342 specifies the on-model position based on the on-model distance corrected by the correction section 3423.

This makes it possible to correct the difference between the moving distance on the guide image and the in vivo moving distance of the endoscope apparatus based on the structural properties of the site.

5. Fourth Embodiment

Figure 28:
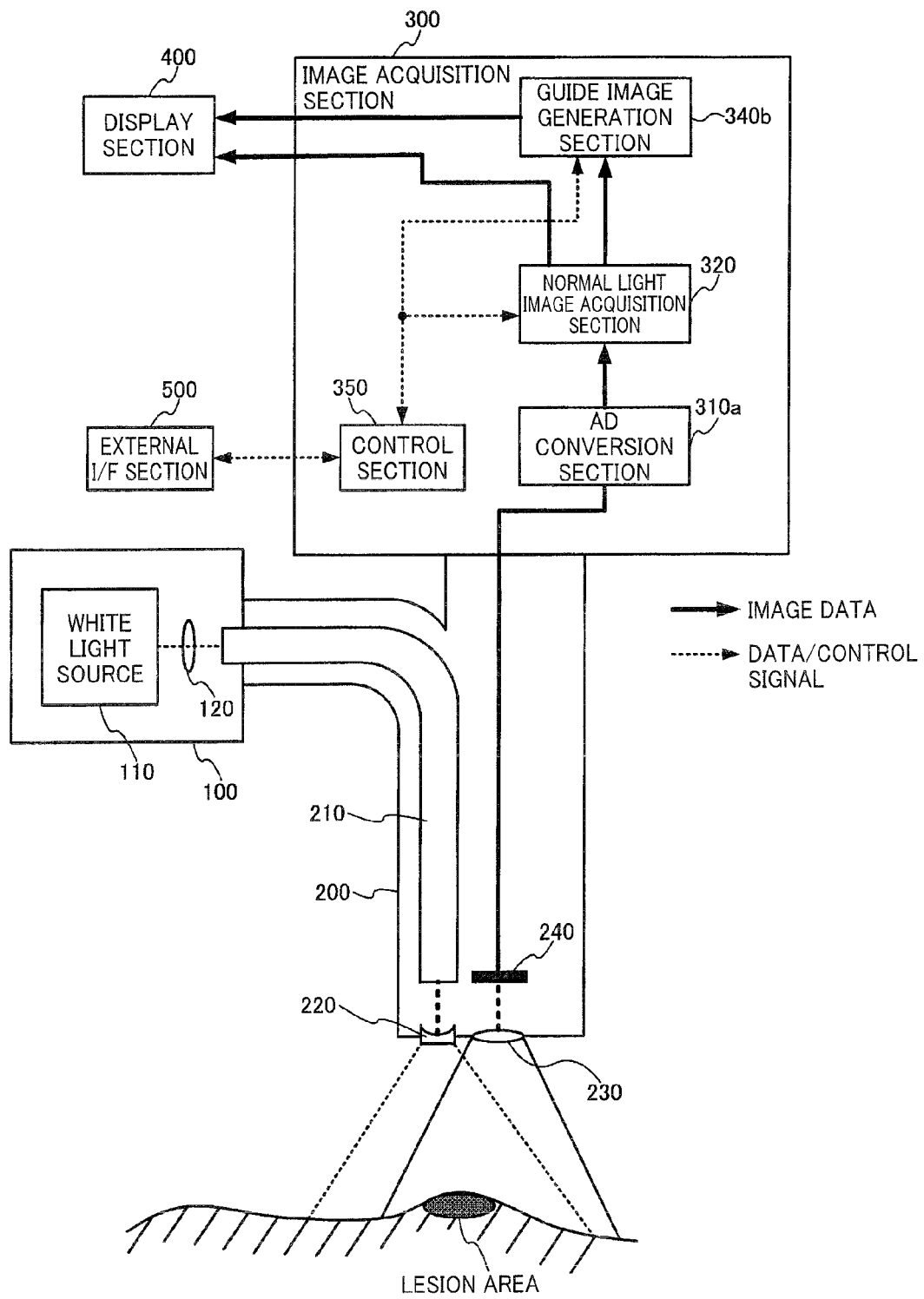
FIG. 28 shows yet another system configuration example according to one embodiment of the invention.

An endoscope apparatus that includes an image processing device according to a fourth embodiment of the invention is described below. FIG. 28 shows the endoscope apparatus according to the fourth embodiment. The endoscope apparatus according to the fourth embodiment differs from the endoscope apparatus according to the first embodiment in that the special light image acquisition block is omitted.

Figure 29:
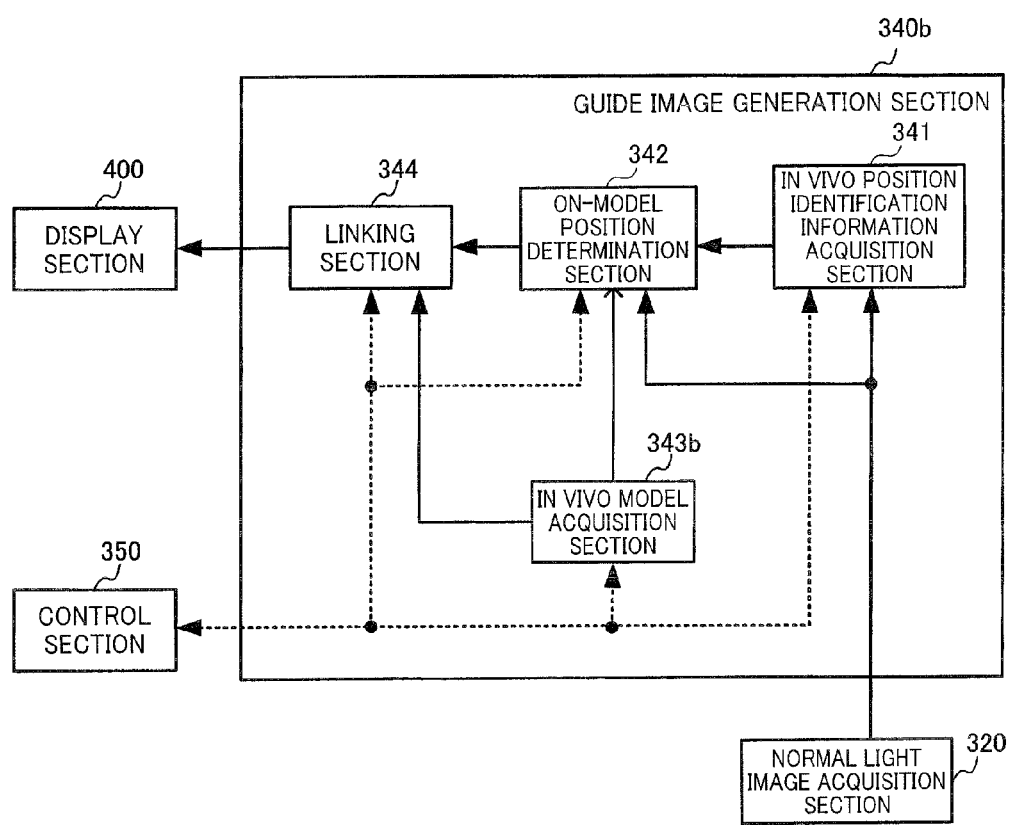
FIG. 29 shows another configuration example of a guide image generation section.

FIG. 29 shows the configuration of a guide image generation section 340b. The guide image generation section 340b differs from the guide image generation section 340 in that the attention area detection section is omitted. The function of an in vivo model acquisition section 343b according to the fourth embodiment differs from that of the in vivo model acquisition section 343 according to the first embodiment.

The in vivo model acquisition section 343b acquires an in vivo model that schematically represents a tissue from a capsule endoscope apparatus under control of the control section 350. The in vivo model acquisition section 343b receives a three-dimensional site model from the capsule endoscope apparatus via a network. The three-dimensional site model is created from a plurality of time-series images acquired in advance from the subject by the capsule endoscope apparatus. When the capsule endoscope apparatus acquires a special light image, a three-dimensional model to which the attention area is linked can be acquired. The three-dimensional site model is output to the model position determination section 342 and the linking section 344.

According to this embodiment, the image processing device includes the attention area detection section 345 that detects the attention area from the acquired image, and the attention area detection section 345 detects the attention area based on the image acquired by the capsule endoscope apparatus.

This makes it possible to detect the attention area (e.g., lesion area) before inserting a normal endoscope apparatus, so that the attention area can be reliably detected when inserting a normal endoscope apparatus. Moreover, the special light image acquisition section can be omitted from the endoscope apparatus.

The in vivo model acquisition section 343 acquires the in vivo model based on the image acquired by the capsule endoscope apparatus.

Therefore, since the in vivo model is acquired from the subject, an accurate site model can be used. An in vivo model to which information about the attention area is linked can be acquired by detecting the attention area using the capsule endoscope apparatus, so that the doctor can more easily make a diagnosis.

6. Fifth Embodiment

An endoscope apparatus that includes an image processing device according to a fifth embodiment of the invention is described below. The function of an in vivo model acquisition section 343b according to the fifth embodiment differs from that of the above site model acquisition section 343b.

The in vivo model acquisition section 343b acquires an in vivo model that schematically represents a tissue from a CT scanner under control of the control section 350. The in vivo model acquisition section 343b receives a three-dimensional site model from the CT scanner via a network. The three-dimensional site model is created by a model fitting method from a plurality of spatially successive slice images acquired in advance from the subject using the CT scanner. Elevations and depressions of the three-dimensional site model are detected, and linked to the in vivo model as the attention area. The three-dimensional site model to which the attention area is linked is output to the model position determination section 342 and the linking section 344.

According to this embodiment, the image processing device includes the attention area detection section 345 that detects the attention area from the acquired site model, and the linking section 344 links information about the attention area to the position of the attention area detected from the in vivo model.

This makes it possible to acquire the in vivo model to which the attention area is linked. Therefore, the endoscope apparatus need not include the special light image acquisition section. Since the in vivo model is acquired from the subject, an accurate site model can be used.

The attention area detection section 345 detects the attention area based on the image acquired by the CT scanner.

This makes it possible to detect the attention area (e.g., lesion area) before inserting a normal endoscope apparatus, so that the attention area can be reliably detected when inserting a normal endoscope apparatus. Moreover, the special light image acquisition section can be omitted from the endoscope apparatus.

The in vivo model acquisition section 343 acquires the in vivo model based on the image acquired by the CT scanner.

Therefore, since the in vivo model is acquired from the subject, an accurate site model can be used. An in vivo model to which information about the attention area is linked can be acquired by detecting the attention area using the CT scanner, so that the doctor can more easily make a diagnosis.

The first to fifth embodiments according to the invention and the modifications thereof have been described above. Note that the invention is not limited to the first to fifth embodiments and the modifications thereof. Various modifications and variations may be made without departing from the scope of the invention. A plurality of elements of each of the first to fifth embodiments and the modifications thereof may be appropriately combined. For example, some elements may be omitted from the elements of the first to fifth embodiments and the modifications thereof. The elements described in connection with the first to fifth embodiments and the modifications thereof may be appropriately combined. Specifically, various modifications and applications are possible without materially departing from the novel teachings and advantages of the invention.

What is claimed is:

1. An image processing device comprising:
a processor; and
a memory storing computer-readable instructions that, when executed by the processor, implement:
an image acquisition section that acquires an image that has been acquired by imaging a tissue using an endoscope apparatus;
an in vivo position and moving distance identification information acquisition section that acquires, based on the acquired image: (a) in vivo position identification information that specifies an in vivo position of the endoscope apparatus when the image has been acquired; and (b) moving distance information that indicates an in vivo moving distance of the endoscope apparatus;
an in vivo model acquisition section that acquires an in vivo model that schematically represents a model of the tissue;
an on-model position determination section that specifies an on-model position that corresponds to the position specified by the in vivo position identification information on the acquired in vivo model; and
a linking section that links information about the acquired image to the specified on-model position;
wherein the in vivo position and moving distance identification information acquisition section includes a correction section that corrects the moving distance information based on structural properties of the entirety or part of a tissue where the endoscope apparatus has moved; and
wherein the on-model position determination section specifies the on-model position that corresponds to the acquired image based on the moving distance information corrected by the correction section.

2. The image processing device as defined in claim 1,
the in vivo position and moving distance identification information acquisition section including a direction information calculation section that calculates moving direction information that indicates an in vivo moving direction of the endoscope apparatus based on the acquired image, and
the in vivo position and moving distance identification information acquisition section acquiring the moving direction information calculated by the direction information calculation section as the in vivo position identification information.

3. The image processing device as defined in claim 1,
the image acquisition section acquiring a first image and a second image,
the first image being acquired at a first timing,
the second image being acquired at a second timing that occurs after the first timing, and
the in vivo position and moving distance identification information section performing a matching process on the first image and the second image, and acquiring the in vivo position identification information based on a result of the matching process.

4. The image processing device as defined in claim 1,
the on-model position determination section including a conversion section that converts the distance indicated by the moving distance information corrected by the correction section into a distance on the in vivo model, and
the on-model position determination section specifying the on-model position that corresponds to the acquired image based on the distance on the in vivo model obtained by the conversion section.

5. The image processing device as defined in claim 4,
the on-model position determination section including a reference position detection section that detects a reference position that indicates a start point of movement of the endoscope apparatus, and
the on-model position determination section specifying a position distant from the reference position detected by the reference position detection section by the distance on the in vivo model as the on-model position that corresponds to the acquired image.

6. The image processing device as defined in claim 5,
the in vivo position and moving distance identification information acquisition section including a direction information calculation section that calculates moving direction information that indicates an in vivo moving direction of the endoscope apparatus,
the conversion section converting the direction indicated by the moving direction information calculated by the direction information calculation section into a moving direction on the in vivo model, and
the on-model position determination section specifying a position that is distant from the reference position detected by the reference position detection section by the distance on the in vivo model in the moving direction on the in vivo model as the on-model position that corresponds to the acquired image.

7. The image processing device as defined in claim 1,
the correction section increasing the distance indicated by the moving distance information when the endoscope apparatus has moved within the entirety or part of a curved tissue that has a curved section.

8. The image processing device as defined in claim 7,
the curved tissue being a large intestine or a small intestine.

9. The image processing device as defined in claim 1,
the on-model position determination section including a conversion section that converts the distance indicated by the moving distance information into a distance on the in vivo model, and
the on-model position determination section specifying the on-model position based on the distance on the in vivo model obtained by the conversion section.

10. The image processing device as defined in claim 9,
the on-model position determination section including a correction section that corrects the distance on the in vivo model obtained by the conversion section based on structural properties of the entirety or part of a tissue where the endoscope apparatus has moved, and
the on-model position determination section specifying the on-model position based on the distance on the in vivo model that has been corrected by the correction section.

11. The image processing device as defined in claim 1,
the on-model position determination section including a reference position detection section that detects a reference position that indicates a start point of movement of the endoscope apparatus, and
the on-model position determination section specifying the on-model position based on the reference position detected by the reference position detection section and the in vivo position identification information.

12. The image processing device as defined in claim 11,
the reference position detection section detecting a measurement start point as the reference position, and
the measurement start point being a point where imaging using the endoscope apparatus has started.

13. The image processing device as defined in claim 11,
the reference position detection section detecting a point where imaging of a given tissue using the endoscope apparatus has started as the reference position.

14. The image processing device as defined in claim 1, wherein the computer-readable instructions, when executed by the processor, further implement a sensor information acquisition section that acquires sensor information from a sensor,
the in vivo position and moving distance identification information acquisition section acquiring movement information about the endoscope apparatus as the in vivo position identification information based on the sensor information acquired by the sensor information acquisition section.

15. The image processing device as defined in claim 14, wherein the computer-readable instructions, when executed by the processor, further implement a display control section that controls display of an in vivo model image and the acquired image,
the in vivo model image being an image of the in vivo model, and
the display control section deforming the in vivo model image based on the movement information.

16. The image processing device as defined in claim 1, wherein the computer-readable instructions, when executed by the processor, further implement an attention area detection section that detects an attention area from the image acquired by the image acquisition section,
the linking section linking information about an attention image to the on-model position specified by the on-model position determination section, and
the attention image being the acquired image that includes the attention area.

17. The image processing device as defined in claim 16,
the image acquisition section acquiring a special light image that includes an object image including information in a wavelength band narrower than that of white light; and
the attention area detection section detecting the attention area based on the special light image.

18. The image processing device as defined in claim 17,
the attention area detection section detecting the attention area based on an image acquired by a capsule endoscope apparatus.

19. The image processing device as defined in claim 1,
the in vivo model acquisition section acquiring the in vivo model based on an image acquired by a capsule endoscope apparatus.

20. The image processing device as defined in claim 1, wherein the computer-readable instructions, when executed by the processor, further implement an attention area detection section that detects an attention area from the acquired in vivo model,
the linking section linking information about the attention area to a position of the attention area detected from the in vivo model.

21. The image processing device as defined in claim 20,
the attention area detection section detecting the attention area based on an image acquired by a CT scanner.

22. The image processing device as defined in claim 20,
the in vivo model acquisition section acquiring the in vivo model based on an image acquired by a CT scanner.

23. The image processing device as defined in claim 1,
the linking section linking an indicator that indicates a position of the endoscope apparatus when the image has been acquired as the information about the acquired image.

24. The image processing device as defined in claim 1,
the image acquisition section acquiring a first image that includes an object image including information in a wavelength band of white light, and a second image that includes an object image including information in a specific wavelength band narrower than that of white light.

25. The image processing device as defined in claim 24,
the first image and the second image being in vivo images, and
the specific wavelength band included in the in vivo image being a wavelength band absorbed by hemoglobin in blood.

26. The image processing device as defined in claim 25,
the specific wavelength band being 390 to 445 nm or 530 to 550 nm.

27. The image processing device as defined in claim 24,
the first image and the second image being in vivo images, and
the specific wavelength band included in the in vivo image being a wavelength band of fluorescence emitted from a fluorescent substance.

28. The image processing device as defined in claim 27,
the specific wavelength band being 490 to 625 nm.

29. The image processing device as defined in claim 24,
the first image and the second image being in vivo images, and
the specific wavelength band included in the in vivo image being an infrared wavelength band.

30. The image processing device as defined in claim 29,
the specific wavelength band being 790 to 820 nm or 905 to 970 nm.

31. An image processing method comprising:
acquiring an image that has been acquired by imaging a tissue using an endoscope apparatus;
acquiring, based on the acquired image: (a) in vivo position identification information that specifies an in vivo position of the endoscope apparatus when the image has been acquired; and (b) moving distance information that indicates an in vivo moving distance of the endoscope apparatus;
acquiring an in vivo model that schematically represents a model of the tissue;
specifying an on-model position that corresponds to the position specified by the in vivo position identification information on the acquired in vivo model;
linking information about the acquired image to the specified on-model position; and
correcting the moving distance information based on structural properties of the entirety or part of a tissue where the endoscope apparatus has moved;
wherein the specifying step specifies the on-model position that corresponds to the acquired image based on the corrected moving distance information.

32. A program that is stored in an information storage medium, the program causing a computer to function as:
an image acquisition section that acquires an image that has been acquired by imaging a tissue using an endoscope apparatus;

an in vivo position and moving distance identification information acquisition section that acquires, based on the acquired image: (a) in vivo position identification information that specifies an in vivo position of the endoscope apparatus when the image has been acquired; and (b) moving distance information that indicates an in vivo moving distance of the endoscope apparatus;

an in vivo model acquisition section that acquires an in vivo model that schematically represents a model of the tissue;

an on-model position determination section that specifies an on-model position that corresponds to the position specified by the in vivo position identification information on the acquired in vivo model; and a linking section that links information about the acquired image to the specified on-model position;

wherein the in vivo position and moving distance identification information acquisition section includes a correction section that corrects the moving distance information based on structural properties of the entirety or part of a tissue where the endoscope apparatus has moved; and wherein the on-model position determination section specifies the on-model position that corresponds to the acquired image based on the corrected moving distance information.

* * * * *